(12) United States Patent
Bureau et al.

(10) Patent No.: US 6,939,862 B2
(45) Date of Patent: Sep. 6, 2005

(54) METHOD FOR TRANSFERRING NUCLEIC ACID INTO STRIATED MUSCLES

(75) Inventors: Michel Bureau, Saint Cloud (FR); Lluis Mir, Verrières le Buisson (FR); Daniel Scherman, Paris (FR)

(73) Assignees: Aventis Pharma S.A., Antony Cedex (FR); Centre National de la Recherche Scientifique, Paris (FR); Institut Gustave Roussy, Villejuif Cedex (FR)

( * ) Notice: Subject to any disclaimer, the term of this patent is extended or adjusted under 35 U.S.C. 154(b) by 213 days.

(21) Appl. No.: 09/986,033

(22) Filed: Nov. 7, 2001

(65) Prior Publication Data

US 2003/0073653 A1 Apr. 17, 2003

Related U.S. Application Data

(63) Continuation of application No. 09/341,350, filed as application No. PCT/FR98/01400 on Jun. 30, 1998, now abandoned.
(60) Provisional application No. 60/067,488, filed on Dec. 1, 1997.

(30) Foreign Application Priority Data

Jun. 30, 1997 (FR) .............................. 97 08233

(51) Int. Cl.$^7$ .............................................. A61K 31/70
(52) U.S. Cl. ........................................................ 514/44
(58) Field of Search ........................................... 514/44

(56) References Cited

U.S. PATENT DOCUMENTS

| 4,411,657 A | 10/1983 | Galindo |
| 4,441,972 A | 4/1984 | Pohl |
| 4,474,570 A | 10/1984 | Ariura et al. |
| 4,476,004 A | 10/1984 | Pohl |
| 4,557,723 A | 12/1985 | Sibalis |
| 4,578,168 A | 3/1986 | Hofmann |
| 4,622,031 A | 11/1986 | Sibalis |
| 4,639,244 A | 1/1987 | Rizk et al. |
| 4,663,292 A | 5/1987 | Wong et al. |
| 4,695,547 A | 9/1987 | Hilliard et al. |
| 4,702,732 A | 10/1987 | Powers et al. |
| 4,764,473 A | 8/1988 | Matschke et al. |
| 4,776,349 A | 10/1988 | Nashef et al. |
| 4,786,277 A | 11/1988 | Powers et al. |
| 5,019,034 A | 5/1991 | Weaver et al. |
| 5,049,488 A | 9/1991 | Baer et al. |
| 5,081,990 A | 1/1992 | Deletis |
| 5,119,832 A | 6/1992 | Xavier |
| 5,124,259 A | 6/1992 | Tada |
| 5,128,257 A | 7/1992 | Baer |
| 5,273,525 A * | 12/1993 | Hofmann ............... 604/21 |
| 5,282,785 A | 2/1994 | Shapland et al. |
| 5,286,254 A | 2/1994 | Shapland et al. |
| 5,304,120 A | 4/1994 | Crandell et al. |
| 5,304,486 A | 4/1994 | Chang |
| 5,318,514 A | 6/1994 | Hofmann |
| 5,371,003 A | 12/1994 | Murray et al. |
| 5,389,069 A | 2/1995 | Weaver |
| 5,425,703 A | 6/1995 | Feiring |
| 5,439,440 A | 8/1995 | Hofmann |
| 5,462,520 A | 10/1995 | Hofmann |
| 5,464,386 A | 11/1995 | Hofmann |
| 5,468,223 A | 11/1995 | Mir |
| 5,499,971 A | 3/1996 | Shapland et al. |
| 5,501,662 A | 3/1996 | Hofmann |
| 5,543,282 A | 8/1996 | Mihayashi et al. |

(Continued)

FOREIGN PATENT DOCUMENTS

| EP | 0 140 308 B2 | 5/1985 | ........... C12N/15/11 |
| EP | 0 185 573 B1 | 6/1986 | ........... C12N/15/36 |
| EP | 0 259 212 B1 | 3/1988 | ........... C12N/15/00 |
| EP | 0 321 201 B1 | 6/1989 | ........... C12N/9/00 |
| FR | 2 681 786 | 4/1993 | ........... A61K/31/70 |
| FR | 2 688 514 | 9/1993 | ........... C12N/15/87 |
| GB | 2113 097 A | 8/1983 | |
| JP | 10-234366 | 8/1998 | |
| WO | WO 89/06555 | 7/1989 | |
| WO | WO 93/06223 | 4/1993 | ........... C12N/15/86 |
| WO | WO 93/19191 A1 | 9/1993 | ........... C12N/15/86 |
| WO | WO 95/23211 | 8/1995 | |
| WO | WO 96/00111 | 1/1996 | |
| WO | WO 96/01414 | 1/1996 | ........... G01L/13/02 |
| WO | WO 96/39226 * | 12/1996 | ........... A61N/1/32 |
| WO | WO 96/39531 | 12/1996 | |
| WO | WO 97/07826 | 3/1997 | |
| WO | WO 97/10343 | 3/1997 | ........... C12N/15/69 |
| WO | WO 98/43702 | 10/1998 | |
| WO | WO 99/06101 | 2/1999 | |
| WO | WO 99/36563 | 7/1999 | |
| WO | WO 00/02621 | 1/2000 | |

OTHER PUBLICATIONS

Aihara et al., "Gene Transfer into Muscle by Electroporation In Vivo," *Nature Biotechnology*, 16, pp. 867–870 (1998).

Gorza et al., "Slow–to–Fast Transformation of Denervated Soleus Muscles by Chronic High–Frequency Stimulation in the Rat," *Journal of Physiology*, 402, pp. 627–649 (1988).

Heller et al., "In Vivo Gene Electroinjection and Expression in Rat Liver," *FEBS Letters*, 389, pp. 225–228 (1996).

(Continued)

*Primary Examiner*—Joseph T. Woitach
(74) *Attorney, Agent, or Firm*—Finnegan, Henderson, Farabow, Garrett & Dunner, LLP

(57) ABSTRACT

The invention provides a method of transferring in vivo a molecule into a striated muscle cell. More specifically, a method of the invention comprises contacting in vivo a striated muscle cell with a molecule, and electrically stimulating the muscle cell with one or more unipolar pulses of an electric field intensity ranging from 1 to 800 V/cm$^2$. In one embodiment, the molecule is a nucleic acid encoding a protein of interest. For example, the invention provides methods of promoting angiogenesis and hemostasis.

30 Claims, 20 Drawing Sheets

U.S. PATENT DOCUMENTS

Figure 1A:
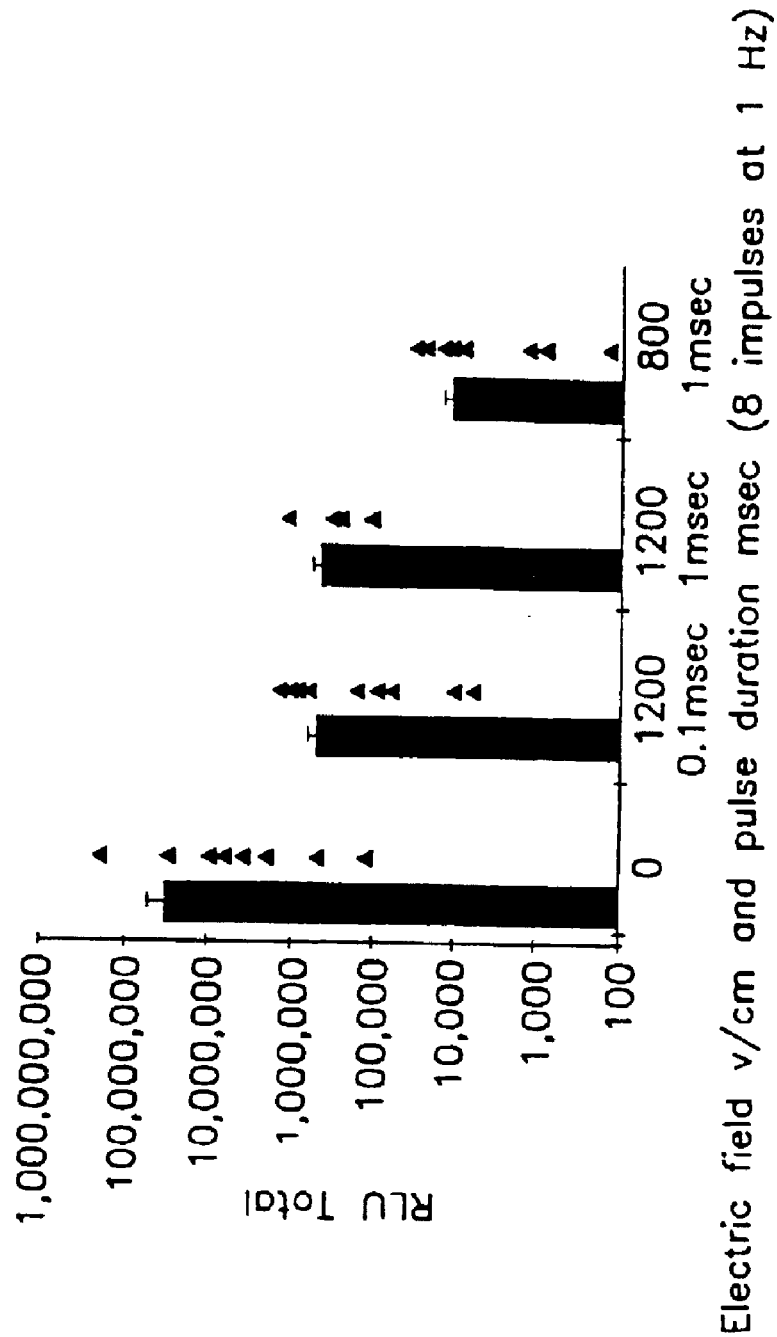

| | | | |
|---|---|---|---|
| 5,589,069 A | 12/1996 | Wenzhi | |
| 5,607,691 A | 3/1997 | Hale et al. | |
| 5,662,944 A | 9/1997 | Petrucco | |
| 5,667,491 A | 9/1997 | Pliquett et al. | |
| 5,674,267 A | 10/1997 | Mir et al. | |
| 5,679,647 A | 10/1997 | Carson et al. | |
| 5,685,274 A | 11/1997 | Helmbrecht et al. | |
| 5,688,233 A | 11/1997 | Hofmann et al. | |
| 5,693,622 A * | 12/1997 | Wolff et al. | 514/44 |
| 5,702,359 A | 12/1997 | Hofmann et al. | |
| 5,744,133 A | 4/1998 | Lathe et al. | 424/93.2 |
| 5,749,847 A | 5/1998 | Zewert et al. | |
| 5,804,566 A | 9/1998 | Carson et al. | |
| 5,810,762 A | 9/1998 | Hofmann | |
| 5,814,603 A | 9/1998 | Oldenburg et al. | |
| 5,849,719 A | 12/1998 | Carson et al. | |
| 5,944,710 A | 8/1999 | Dev et al. | |
| 5,944,726 A | 8/1999 | Blaeser et al. | |
| 5,960,974 A | 10/1999 | Kee et al. | |
| 5,993,434 A * | 11/1999 | Dev et al. | 604/501 |
| 6,007,806 A | 12/1999 | Lathe et al. | 424/93.2 |
| 6,014,584 A | 1/2000 | Hofmann et al. | |
| 6,055,453 A | 4/2000 | Hofmann et al. | |
| 6,110,161 A | 8/2000 | Mathiesen et al. | |
| 6,228,844 B1 * | 5/2001 | Wolff et al. | 514/44 |
| 6,241,701 B1 * | 6/2001 | Hofmann | 604/21 |
| 6,426,216 B1 | 7/2002 | Perricaudet et al. | 435/320.1 |
| 6,678,556 B1 | 1/2004 | Nolan et al. | 604/21 |
| 6,696,420 B1 | 2/2004 | Perricaudet et al. | 514/44 |
| 2002/0099323 A1 * | 7/2002 | Dev et al. | 604/21 |

OTHER PUBLICATIONS

Kim et al., "Electroporation of Extraneous Proteins into CHO Cells: Increased Efficacy by Utilizing Centrifugal Force and Microsecond Electrical Pulses," *Experimental Cell Research*, 197, pp. 207–212 (1991).

Lee et al., "Surfactant–induced Sealing of Electropermeabilized Skeletal Muscle Membranes in Vivo," *Proc. Natl. Acad. Sci. USA*, 89, pp. 4524–4528 (1992).

Mathiesen et al., "Regulation of the Size and Distribution of Agrin–Induced Postsynaptic–like Apparatus in Adult Skeletal Muscle by Electrical Muscle Activity," *Molecular and Cellular Neuroscience*, 13, pp. 207–217 (1999).

Mathiesen, I., "Electropermeabilization of Skeletal Muscle Enhances Gene Transfer In Vivio," *Gene Therapy*, 5, pp. 508–514 (1999).

Nishi et al., "High–Efficiency In Vivo Gene Transfer Using Intraarterial Plasmid DNA Injection Following In Vivo Electroporation," *Cancer Research*, 56, pp. 1050–1055 (1996).

Rizzuto et al., "Efficient and Regulated Erythropoietin Production by Naked DNA Injection and Muscle Electroporation," *Proc. Natl. Acad. Sci. USA*, 96, pp. 6417–6422 (1999).

Rols et al., "In Vivo Electrically Mediated Protein and Gene Transfer in Murine Melanoma," *Nature Biotechnology*, 16, pp. 168–170 (1998).

Rols et al., "Highly Efficient Transfection of Mammalian Cells by Electric Field Pulses," *Eur. J. Biochem.* 206, pp. 115–121 (1992).

Sixou et al., "Optimized Conditions for Electrotransformation of Bacteria are Related to the Extent of Electropermeabilization," *Biochimica et Biophysica Acta*, 1088, pp. 135–138 (1991).

Tatham et al., "ATP–induced Pore Formation in the Plasma Membrane of Rat Peritoneal Mast Cells," *J. Gen. Physiol.*, 95, pp. 459–476 (1990).

Teissie et al., "An Experimental Evaluation of the Critical Potential Difference Inducing Cell Membrane Electropermeabilization," *Biophysical Journal*, 65, pp. 409–413 (1993).

Titomirov et al., "In Vivo Electroporation and Stable Transformation of Skin Cells of Newborn Mice by Plasmid DNA," *Biochimica et Biophysica Acta*, 1088, pp. 131–134 (1991).

Tsurumi et al., "Direct Intramuscular Gene Transfer Of Naked DNA Encoding Vascular Endothelial Growth Factor Augments Collateral Development Tissue Perfusion", *Circulation*, 94(12), pp. 3281–3290 (1996).

J.–P. Behr et al. "Efficient Gene Transfer into Mammalian Primary Endocrine Cells with Lipopolyamine–coated DNA," *Proc. Natl. Acad. Sci. USA* 86:6982–6986 (1989).

O. Boussif et al. "A Versitile Vector for Gene and Oligonucleotide Transfer into Cells in Culture and in Vivo: Polyethylenimine," *Proc. Natl. Acad. Sci. USA* 92:7297–7301 (1995).

I. Danko et al. "Pharmacological Enhancement of in Vivo Foreign Gene Expression in Muscle," *Gene Therapy* 1:114–121 (1994).

H.L. Davis et al. "Direct Gene Transfer into Skeletal Muscle in Vivo: Factors Affecting Efficiency of Transfer and Stability of Expression," *Human Gene Therapy* 4:151–159 (1993).

H.L. Davis et al. "DNA Vaccine for Hepatitis B: Evidence for Immunogenicity in Chimpanzees and Comparison with Other Vaccines," *Proc. Natl. Acad. Sci. USA* 93:7213–7218 (1996).

P.L. Felgner et al. "Lipofection: A Highly Efficient, Lipid–Mediated DNA–transfection Procedure," *Proc. Natl. Acad. Sci. USA* 84:7413–7417 (1987).

J. Jouanneau et al. "Secretred or Nonsecreted Forms of Acidic Fibroblast Growth Factor Produced by Transfected Epithelial Cells Influence Cell Morphology Motility, and Invasive Potential," *Proc. Natl. Acad. Sci. USA* 88:2893–2897 (1991).

M. Manthorpe et al. "Gene Therapy by Intramuscular Injection of Plasmid DNA: Studies on Firefly Luciferase Gene Expression in Mice," *Human Gene Therapy* 4:419–431 (1993).

L.M Mir et al. "Electrochemotherapy Potentiation of Antitumour Effect of Bleomycin by Local Electric Pulses," *Eur. J. Cancer* 27(1):68–72 (1991).

R.J. Mumper et al. "Polyvinyl Derivatives as Novel Interactive Polymers for Controlled Gene Delivery to Muscle," *Pharmaceutical Research* 13(5):701–709 (1996).

P. Nouvel et al. "The Spread of a Replication–Competent MuLV Retroviral Vector can be Efficiently Blocked by Deletion Variants" *Virology* 204:180–189 (1994).

R.S. Williams et al. "Introduction of Foreign Genes into Tissues of Living Mice by DNA–Coated Microprojectiles," *Proc. Natl. Acad. Sci. USA* 88:2726–2730 (1991).

B. Schwartz et al. "Gene Transfer by Naked DNA into Adult Mouse Brain," *Gene Therapy* 3:405–411 (1996).

M. Vitadello et al. "Gene Transfer in Regenerating Muscle," *Human Gene Therapy* 5:11–18 (1994).

P. Wils et al. "Efficient Purification of Plasmid DNA for Gene Transfer Using Triple–Helix Affinity Chromatography," *Gene Therapy* 4:323–330 (1997).

J.A. Wolff et al. "Direct Gene Transfer into Mouse Muscle in Vitro," *Science* 247:1465–1468 (1990).

J.A. Wolff et al. "Conditions Affecting Direct Gene Transfer into Rodent Muscle in Vivo," *BioTechniques* 11(4):474–485 (1991).

N. Saidenberg–Kermanac'h et al. "Efficacy of Interleukin–10 Gene Electrotransfer into Skeletal Muscle in Mice with Collagen–Induced Arthritis," *J. Gene Med.* 5:164–171 (2003).

V. Deleuze et al. "LPS–induced Bronchial Hyperreactivity: Interference by MlL–10 Differs According to Site of Delivery," *Am. J. Physiol. Lung Cell Mol. Physiol.* 286:L98–L105 (2004).

P.–F. Pradat et al. "Viral and Non–viral Gene Thearpy Partially Prevents Experimental Cisplatin–induced Neuropathy," *Gene Therapy* 9:1333–1337 (2002).

M.F. Bureau and D. Scherman "Plasmid DNA Electrotransfer: A New Non Viral Method for Gene Therapy in Oncology,"*Technology in Cancer Research and Treatment* 1(2):149–152 (2002).

J.T. Vilquin et al. "Electrotransfer of Naked DNA in the Skeletal Muscles of Animal Models of Muscular Dystrophies," *Gene Therapy* 8:1097–1107 (2001).

H. Gollins et al. "High–efficiency Plasmid Gene Transfer into Dystrophic Muscle," *Gene Therapy* 10:504–512 (2003).

E. Payen et al. "Improvement of Mouse β–thalassemia by Electrotransfer or Erythropoietin cDNA," *Experimental Hematology* 29:295–300 (2001).

M. Faria et al. "Phosphoramidate Oligonucleotides as Potent Antisense Molecules in Cells and in vivo," *Nature Biotechnology* 19:40–44 (2001).

M. Bachy et al. "Electric Pulses Increase the Immunogenicity of an Influenza DNA Vaccine Injected Intramuscularly in the Mouse," *Vaccine* 19:1688–1693 (2001).

J.–S. Silvestre et al. "Antiangiogenic Effect of Interleukin–10 in Ischemia–Induced Angiogenesis in Mice Hindlimb," *Circulation Research* 87:448–452 (2000).

M. Bettan et al. "High–Level Protein Secretion into Blood Circulation after Electric Pulse–Mediated Gene Transfer into Skeletal Muscle," *Molecular Therapy* 2(3):204–210 (2000).

P. Kreiss et al. "Erythropoietin Secretion and Physiological Effect in Mouse After Intramuscular Plasmid DNA Electrotransfer," *J. Gene Med.* 1:245–250 (1999).

M.F. Bureau et al. "Intramuscular Plasmid DNA Electrotransfer Biodistribution and Degradation," *Biochimica et Biophysica Acta* 1676:138–148 (2004).

P. Bigey er al. "In vivo Plasmid DNA Electrotransfer," *Current Opinion in Biotechnology* 13:443–447 (2002).

D. Scherman et al. "Applications of Plasmid Electrotransfer," *Technology in Cancer Research and Treatment* 1(5):351–354 (2002).

S. Satkauskas et al. "Mechanisms of in Vivo DNA Electrotransfer: Respective Contributions of Cell Electropermeabilization and DNA Electrophoresis," *Molecular Therapy* 5(2):133–140 (2000).

M.F. Bureau et al. "Importance of Association Between Permeabilization and Electrophoretic Forces for Intramuscular DNA Electrotransfer," *Biochimica et Biophysica Acta* 1474:353–359 (2000).

L.M. Mir et al. "High–Efficiency Gene Transfer into Skeletal Muscle Mediated by Electric Pulses," *Proc. Natl. Acad. Sci. USA* 96:4262–4267 (1999).

L.M. Mir et al. "Long–term, High Level in vivo Gene Expression After Electric pulse–mediated Gene Transfer into Skeletal Muscle," *Life Sciences* 321:893–899 (1998).

J.M. Wells et al. "Electroporation–enhanced Gene Delivery in Mammary Tumors," *Gene Therapy* 7:541–547 (2000).

R. Gilbert et al. "Electric Field Enhanced Plasmid Delivery to Liver Hepatocellular Carcinomas," *Technology in Cancer Research and Treatment* 1(5):355–363 (2002).

\* cited by examiner

Figure 1B:
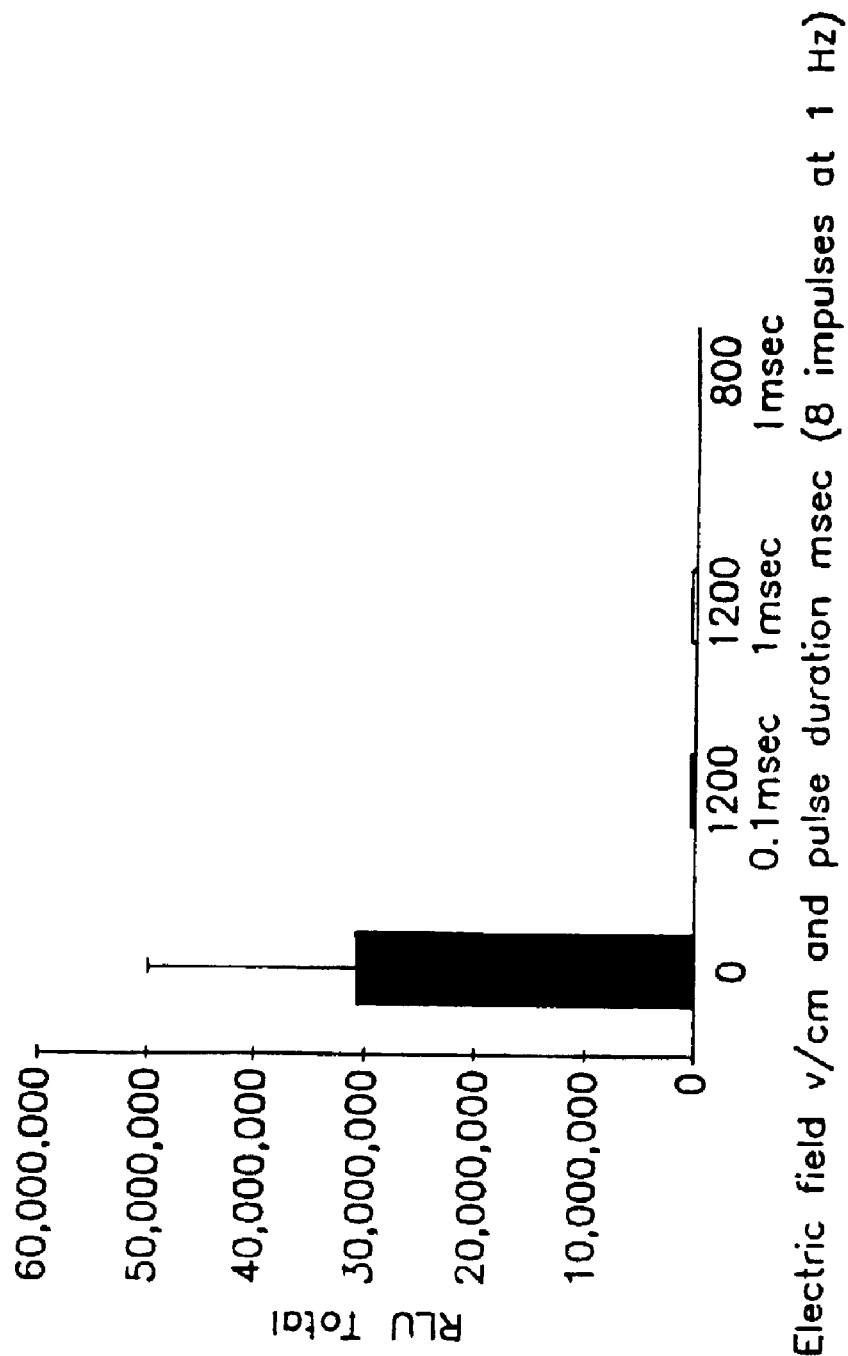

Figure 1: Effects of electric impulses of high field intensity on the transfection of plasmid DNA pxl 2774 in the cranial tibial muscle in the mouse. Mean values ± SEM.

A. Logarithmic scale

Figure 1: Effects of electric impulses of high field intensity on the transfection of plasmid DNA pxl 2774 in the cranial tibial muscle in the mouse. Mean values ± SEM.

B. Linear scale

Figure 2A:
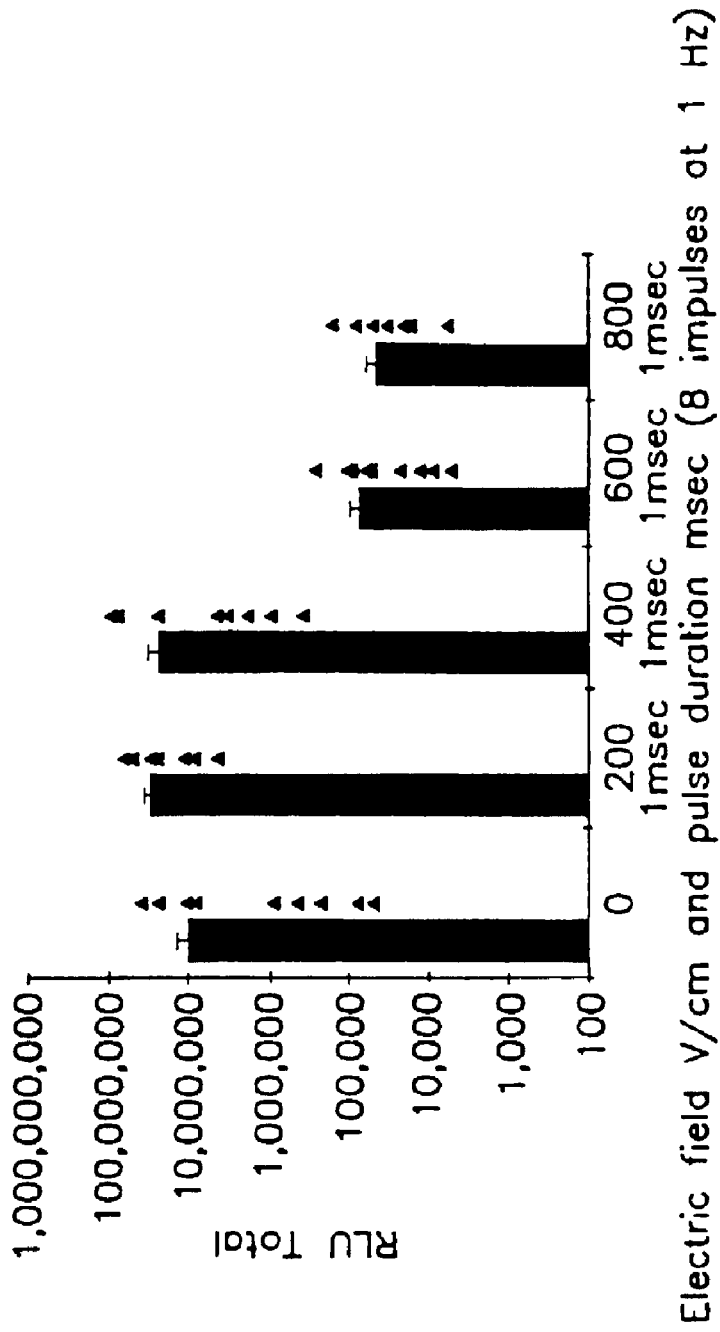
Figure 2B:
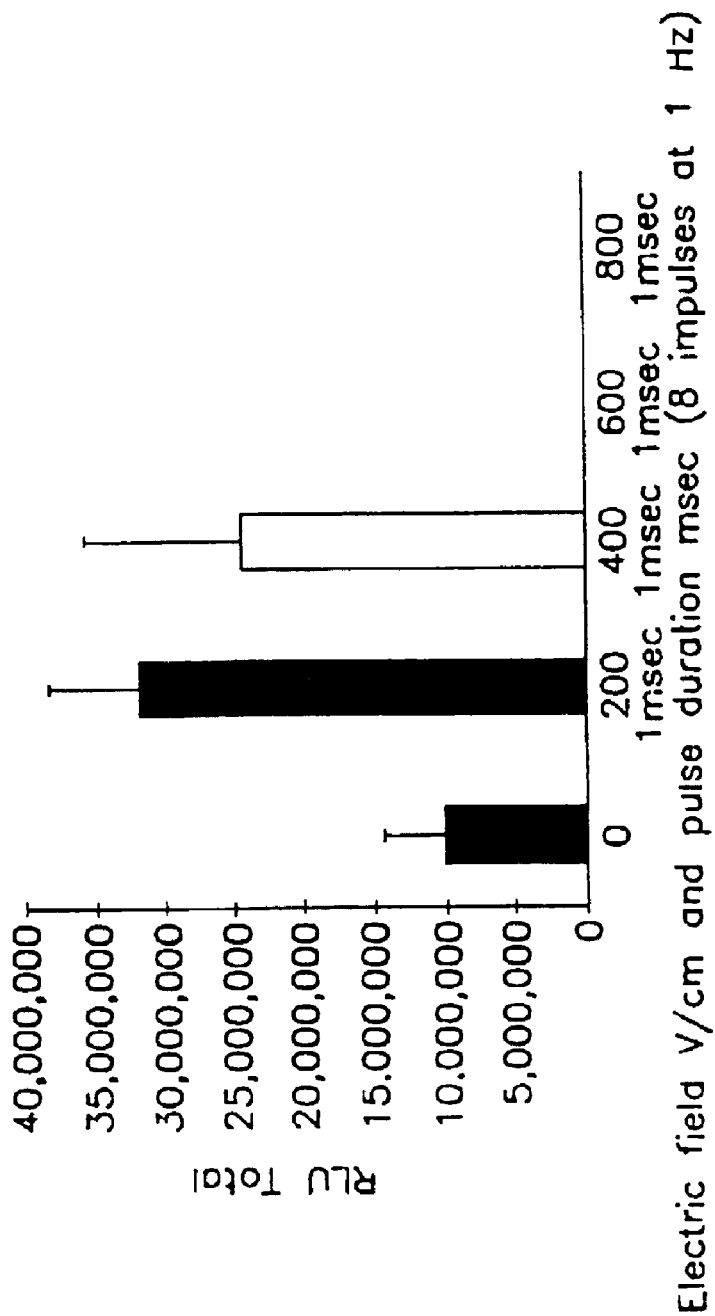

Figure 2: Effects of electric impulses of intermediate field intensity on the transfection of plasmid DNA pxl 2774 in the cranial tibial muscle in the mouse. Mean values ± SEM.

A. Logarithmic scale

Figure 2: Effects of electric impulses of intermediate field intensity of plasmid DNA pxl 2774 in the cranial tibial muscle in the mouse. Mean values ± SEM.

B. Linear scale

Figure 3A:
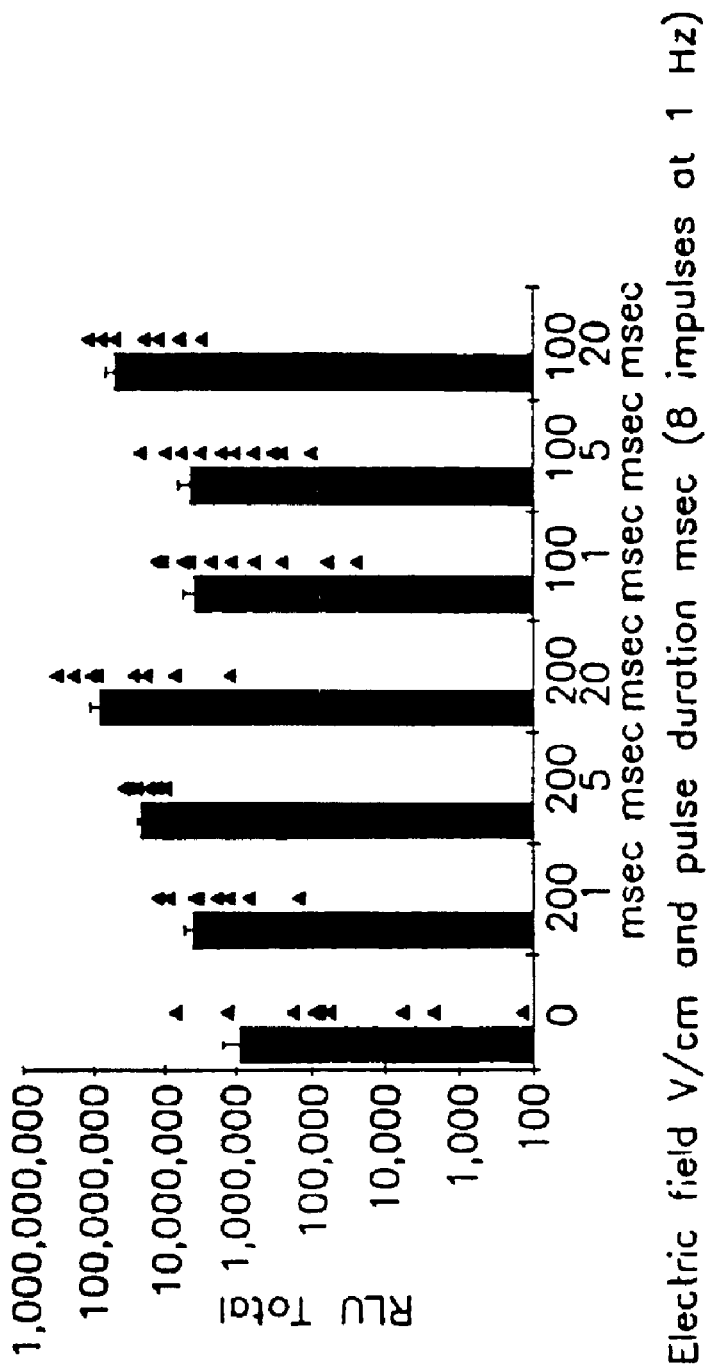
Figure 3B:
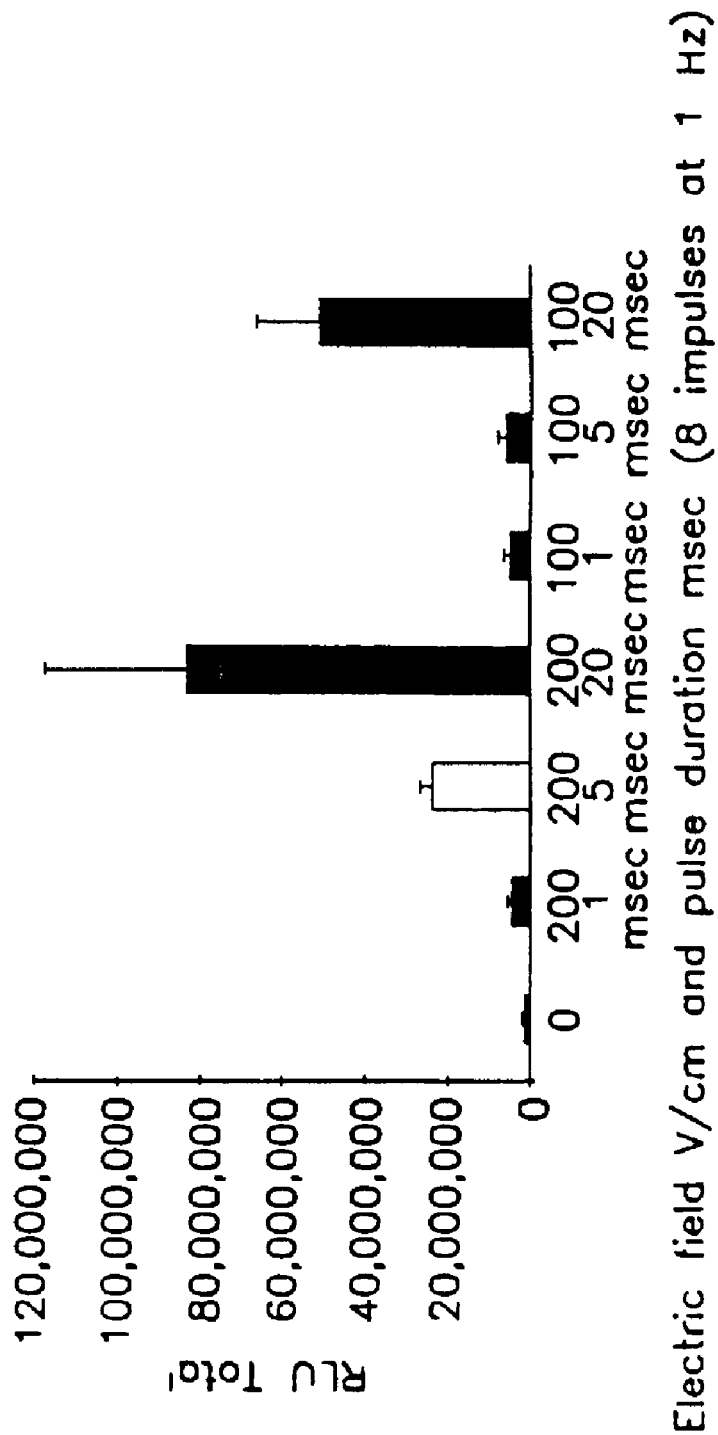

Figure 3: Effects of electric impulses of weak field intensity and of different durations on the transfection of plasmid DNA pxl 2774 in the cranial tibial muscle in the mouse. Mean values ± SEM.

A. Logarithmic scale

Figure 3: Effects of electric impulses of weak field intensity and of different durations on the transfection of plasmid DNA pxl 2774 in the cranial tibial muscle in the mouse. Mean values ± SEM.

B. Linear scale

Figure 4A:
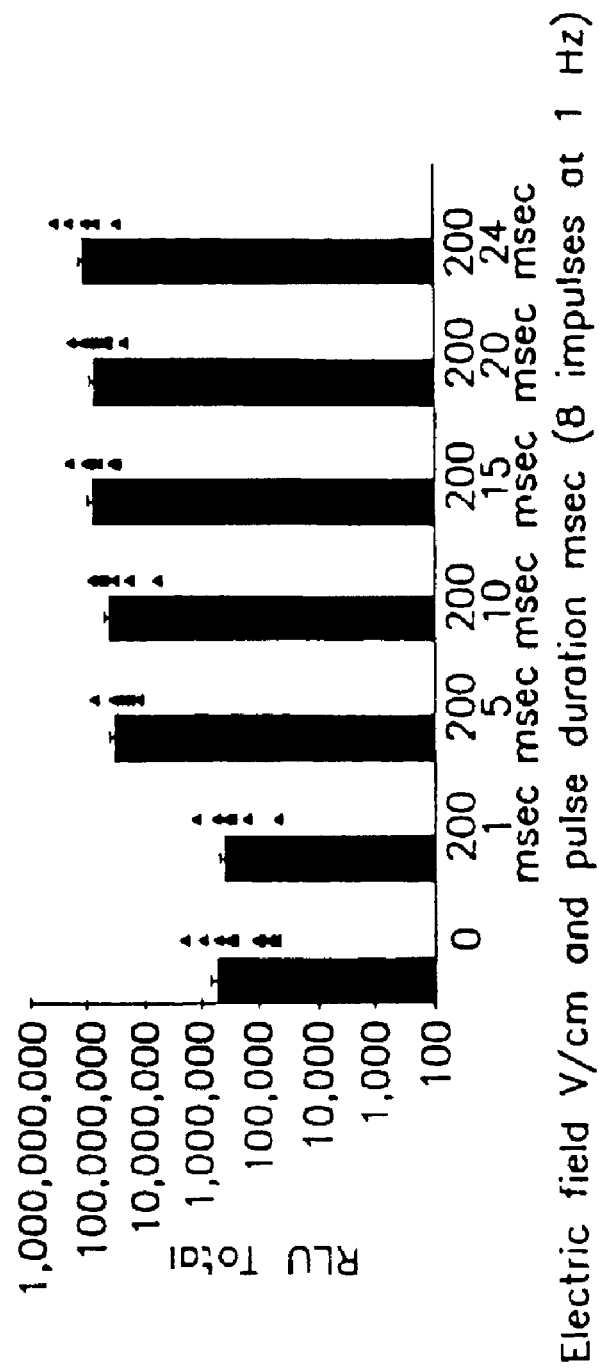
Figure 4B:
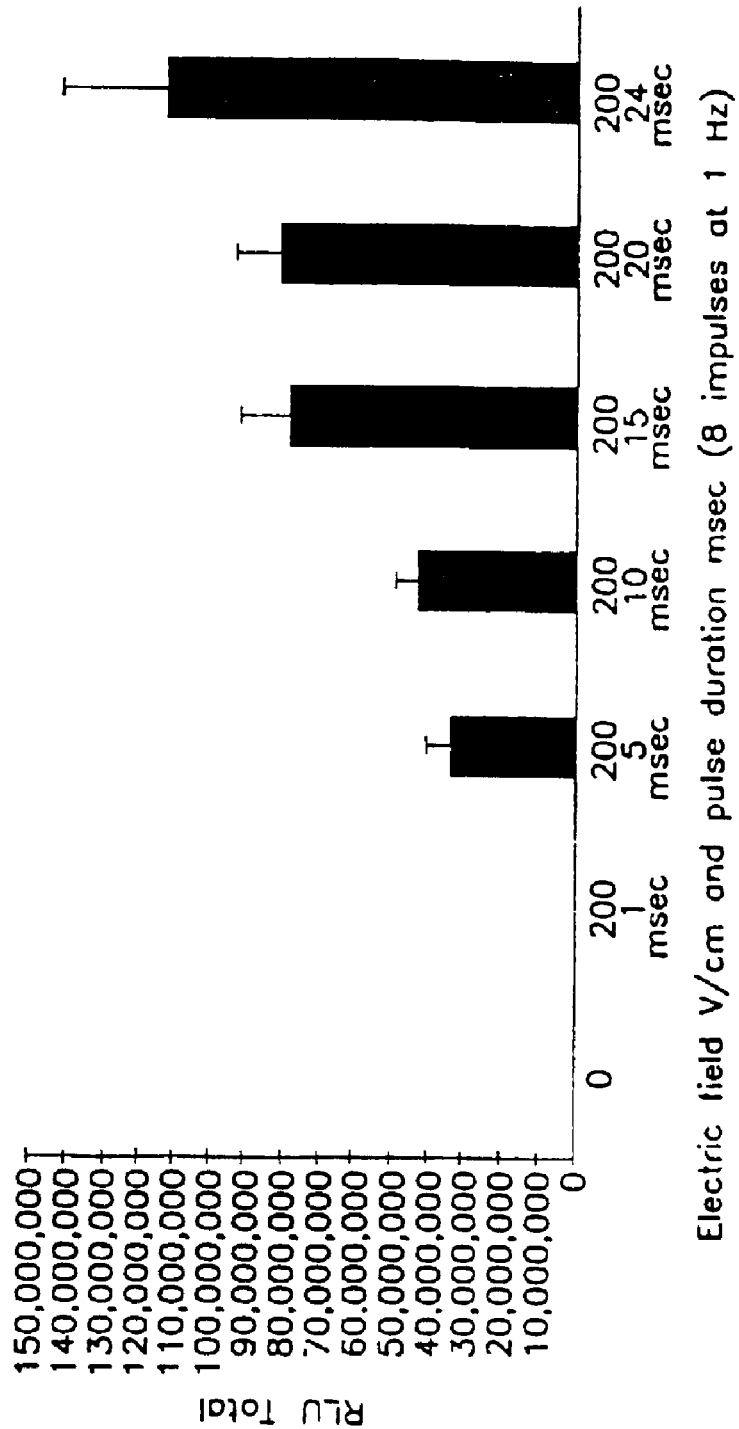

Figure 4: Effects of electric impulses of weak field intensity and of different durations on the transfection of plasmid DNA pxl 2774 in the cranial tibial muscle in the mouse. Mean values ± SEM.

A. Logarithmic scale

Figure 4: Effects of electric impulses of weak field intensity and of different durations on the transfection of plasmid DNA pxl 2774 in the cranial tibial muscle in the mouse. Mean values ± SEM.

B. Linear scale

Figure 5: Effectiveness of electrotransfection of plasmid DNA pxl 2774 in the cranial tibial muscle of the mouse at low electric field intensities. Mean values ± SEM.
Luciferase expression in relation to the mean value of the control group (DNA alone) which was standardized at 1.
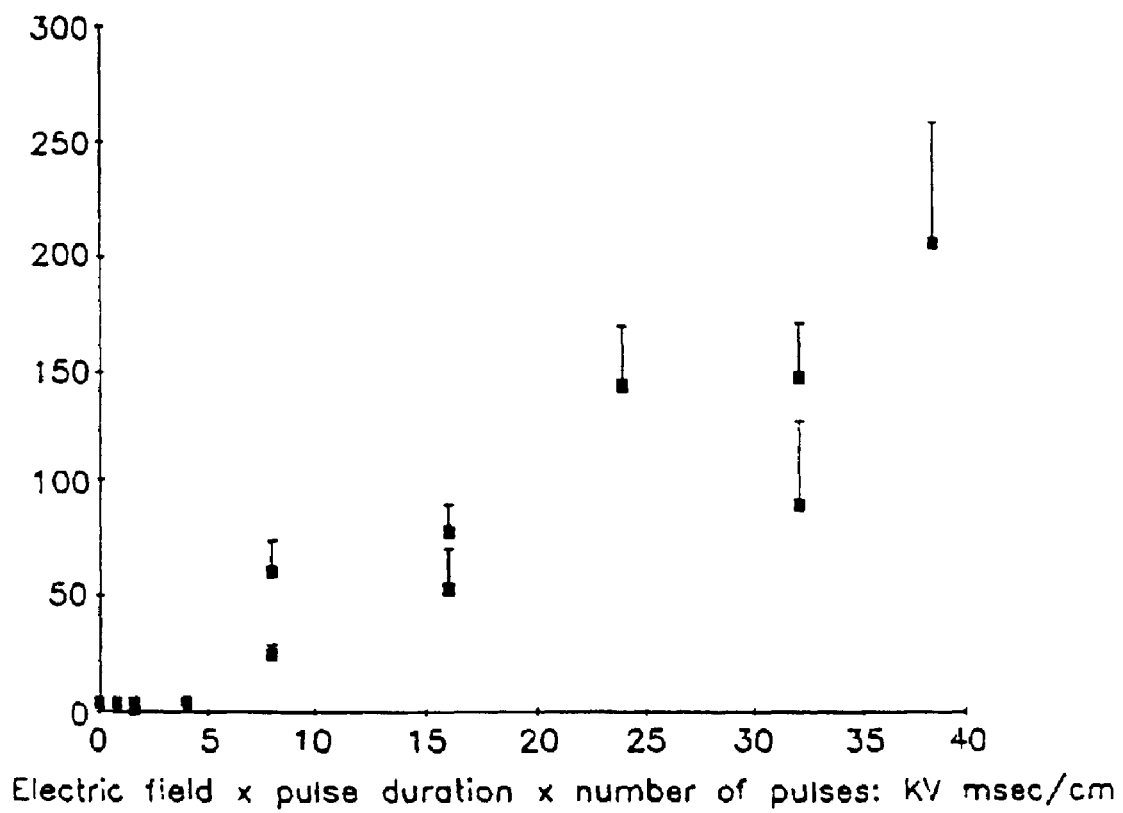

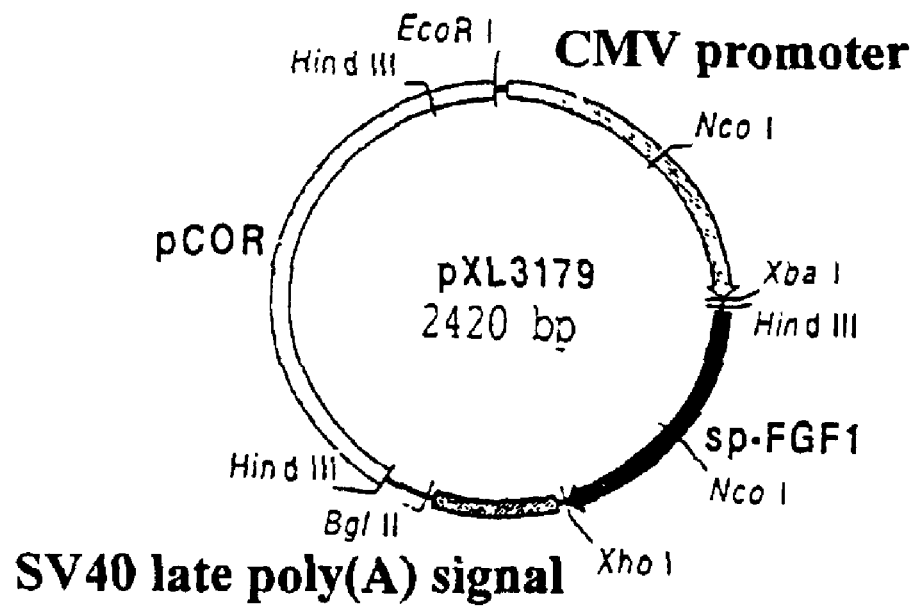
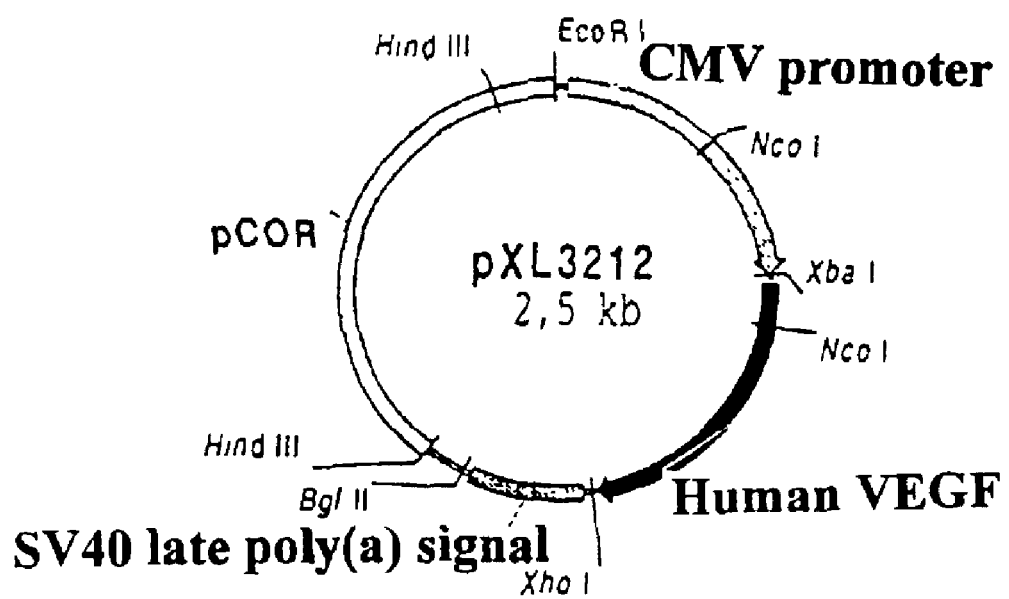
Figure 11

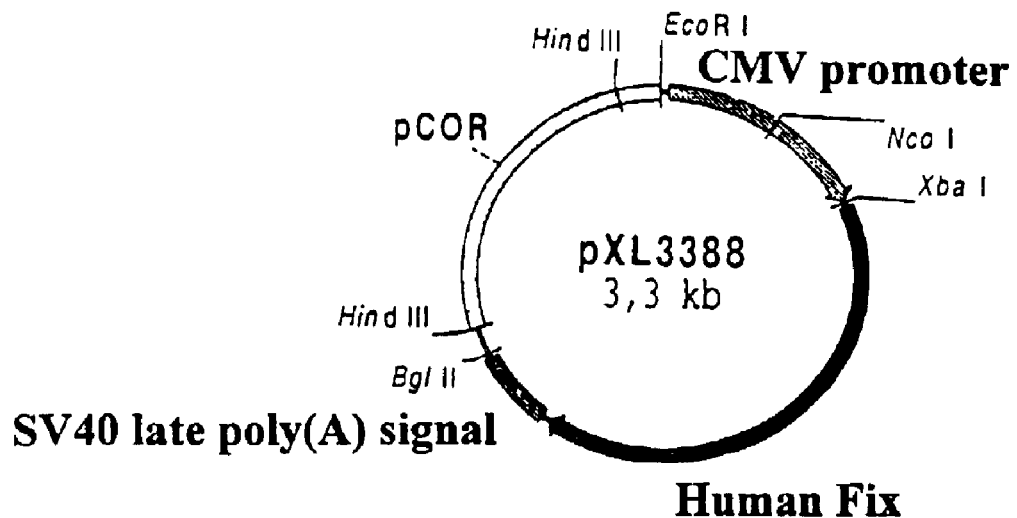
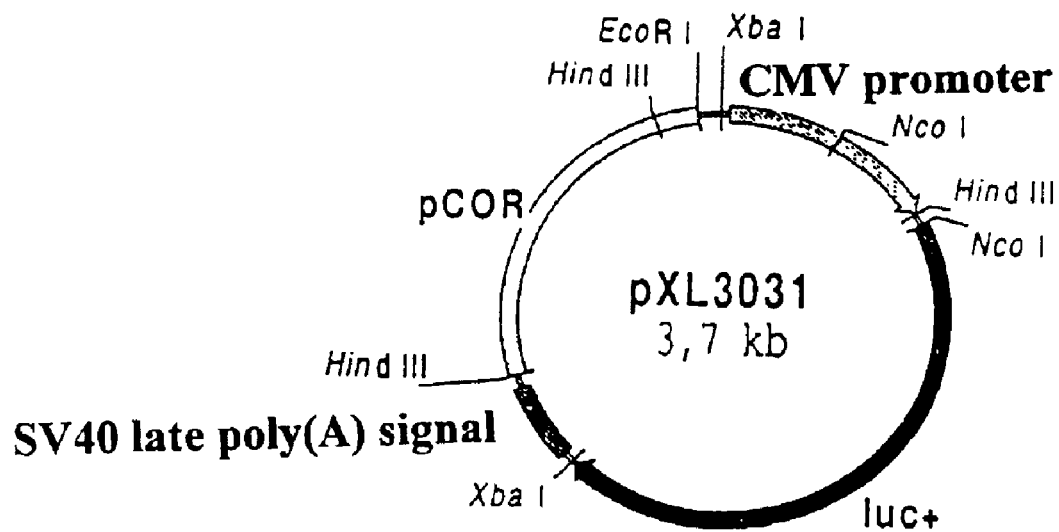
Figure 12

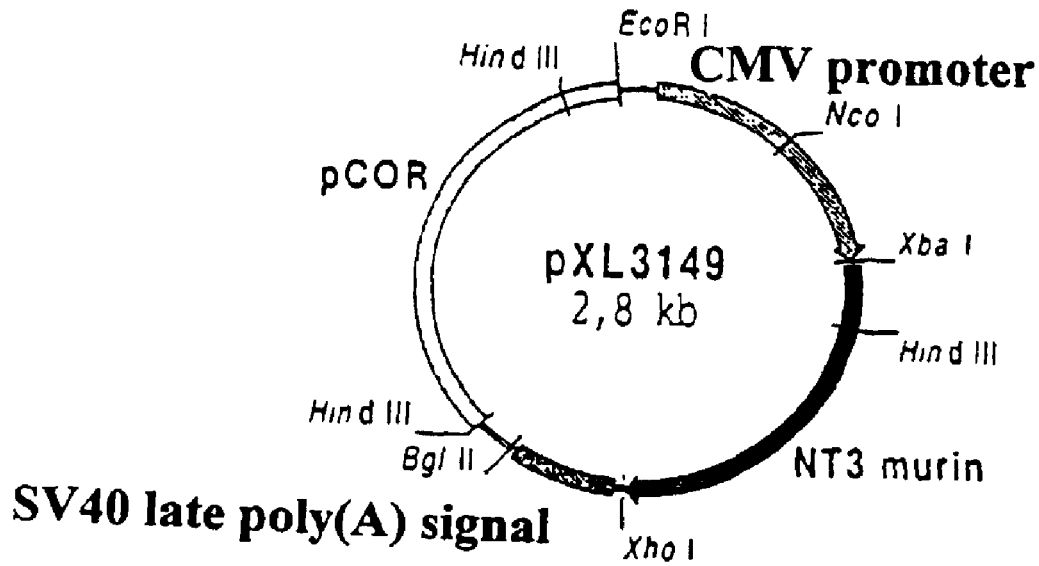
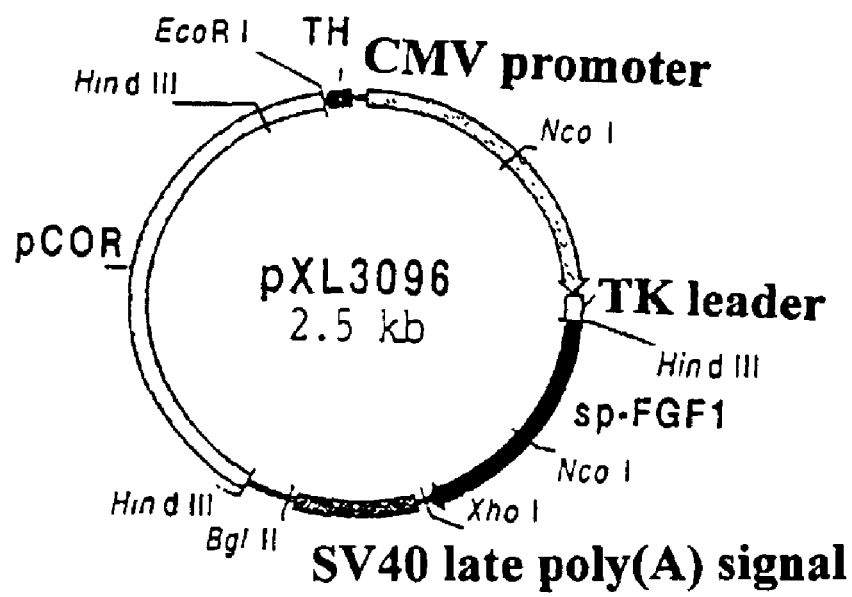
FIGURE 14

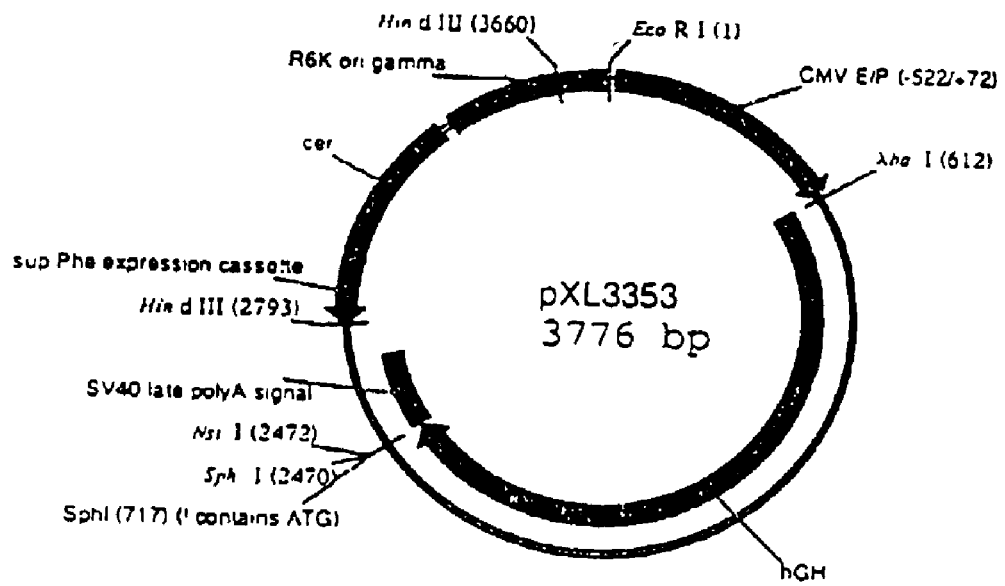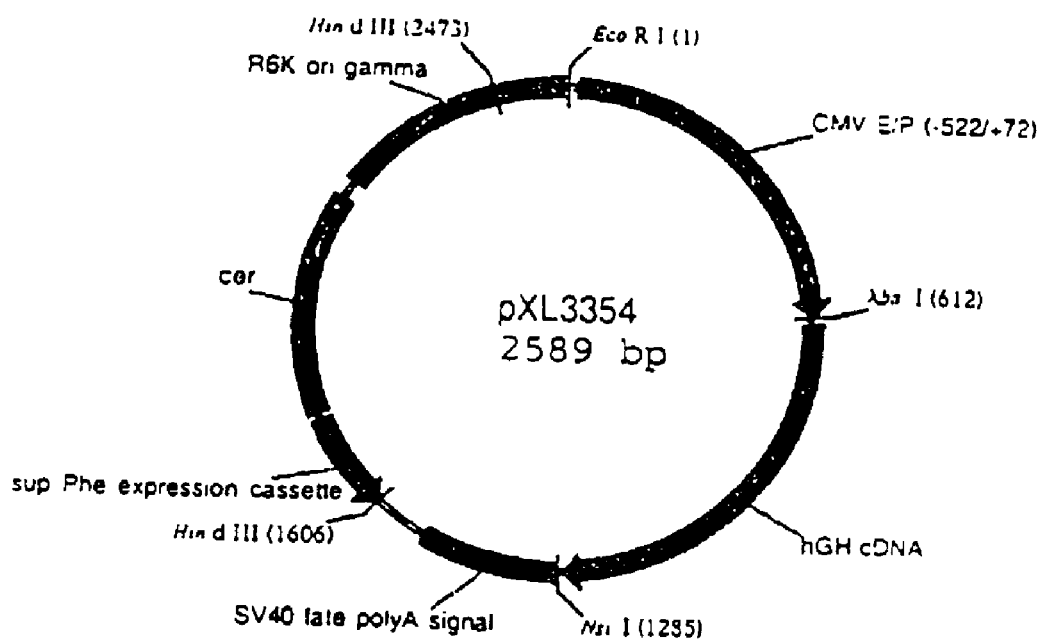
Figure 15

SEQUENCE LISTING

<160> NUMBER OF SEQ ID NOS: 2

<210> SEQ ID NO 1
<211> LENGTH: 35
<212> TYPE: DNA
<213> ORGANISM: Artificial Sequence
<220> FEATURE:
<223> OTHER INFORMATION: Primer

<400> SEQUENCE: 1
gggtctagag ccaccatggc tacaggctcc cggac                                    35

<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
gggatgcatt tactagaagc cacagctgcc tc                                       32

METHOD FOR TRANSFERRING NUCLEIC ACID INTO STRIATED MUSCLES

This application is a continuation of application Ser. No. 09/341,350, filed Jul. 9, 1999, now abandoned, which is the National Stage of International Application PCT/FR98/01400, filed Jun. 30, 1998, which claims priority to U.S. provisional Application No. 60/067,488, filed Dec. 1, 1997. This application also claims priority to French Application No. 97/08233, filed Jun. 30, 1997.

The present invention relates to a very remarkable improvement in the in vivo transfer into striated muscle cells of nucleic acids or of nucleic acids combined with products which make it possible to increase the yield of such transfers, and to the combination of a nucleic acid and the method of transfer according to the invention for their use for gene therapy.

The transfer of genes into a given cell is at the root of gene therapy. However, one of the problems is to succeed in causing a sufficient quantity of nucleic acid to penetrate into cells of the host to be treated; indeed, this nucleic acid, in general a gene of interest, has to be expressed in transfected cells. One of the approaches selected in this regard has been the integration of the nucleic acid into viral vectors, in particular into retroviruses, adenoviruses or adeno-associated viruses. These systems take advantage of the cell penetration mechanisms developed by viruses, as well as their protection against degradation. However, this approach has disadvantages, and in particular a risk of production of infectious viral particles capable of dissemination in the host organism, and, in the case of retroviral vectors, a risk of insertional mutagenesis. Furthermore, the capacity for insertion of a therapeutic or vaccinal gene into a viral genome remains limited.

In any case, the development of viral vectors capable of being used in gene therapy requires the use of complex techniques for defective viruses and for complementation cell lines.

Another approach (Wolf et al. Science 247, 1465–68, 1990; Davis et al. Proc. Natl. Acad. Sci. USA 93, 7213–18, 1996) has therefore consisted in administering into the muscle or into the blood stream a nucleic acid of a plasmid nature, combined or otherwise with compounds intended to promote its transfection, such as proteins, liposomes, charged lipids or cationic polymers such as polyethylenimine, which are good transfection agents in vitro (Behr et al. Proc. Natl. Acad. Sci. USA 86, 6982-6, 1989; Felgner et al. Proc. Natl. Acad. Sci. USA 84, 7413-7, 1987; Boussif et al. Proc. Natl. Acad. Sci. USA 92, 7297-301, 1995).

Since the initial publication by J. A. Wolff et al. showing the capacity of muscle tissue to incorporate DNA injected in free plasmid form (Wolff et al. Science 247, 1465–1468, 1990), numerous authors have tried to improve this procedure (Manthorpe et al., 1993, Human Gene Ther. 4, 419–431; Wolff et al., 1991, BioTechniques 11, 474–485). A few trends emerge from these tests, such as in particular:

the use of mechanical solutions to force the entry of DNA into cells by adsorbing the DNA onto beads which are then propelled onto the tissues ("gene gun") (Sanders Williams et al., 1991, Proc. Natl. Acad. Sci. USA 88, 2726–2730; Fynan et al., 1993, BioTechniques 11, 474–485). These methods have proved effective in vaccination strategy but they affect only the top layers of the tissues. In the case of the muscle, their use would require a surgical approach in order to allow access to the muscle because the particles do not cross the skin tissues;

the injection of DNA, no longer in free plasmid form but combined with molecules capable of serving as vehicle facilitating the entry of the complexes into cells. Cationic lipids, which are used in numerous other transfection methods, have proved up until now disappointing as regards application into the muscle tissue, because those which have been tested have been found to inhibit transfection (Schwartz et al., 1996, Gene Ther. 3, 405–411). Likewise for cationic peptides and polymers (Manthorpe et al., 1993, Human Gene Ther. 4, 419–431). The only case of a favourable combination appears to be the mixing of poly(vinyl alcohol) or polyvinylpyrrolidone with DNA. The increase resulting from these combinations only represents a factor of less than 10 compared with DNA injected in naked form (Mumper et al., 1996, Pharmaceutical Research 13, 701–709);

the pretreatment of the muscle to be injected with solutions intended to improve the diffusion and/or the stability of DNA (Davis et al., 1993, Hum. Gene Ther. 4, 151–159), or to promote the entry of nucleic acids, for example the induction of cell multiplication or regeneration phenomena. The treatments have involved in particular the use of local anaesthetics or of cardiotoxin, of vasoconstrictors, of endotoxin or of other molecules (Manthorpe et al., 1993, Human Gene Ther. 4, 419–431; Danko et al., 1994, Gene Ther. 1, 114–121; Vitadello et al., 1994, Hum. Gene Ther. 5, 11–18). These pretreatment protocols are difficult to manage, bupivacaine in particular requiring, in order to be effective, being injected at doses very close to lethal doses. The preinjection of hyperosmotic sucrose, intended to improve diffusion, does not increase the transfection level in the muscle (Davis et al., 1993).

Electroporation, or use of electric fields to permeabilize cells, is also used in vitro to promote the transfection of DNA into cells in culture. However, it has up until now been accepted that this phenomenon responded to an effect which is dependent on a threshold and that this electropermeabilization could only be observed for electric fields of relatively high intensity, of the order of 800 to 1200 volts/cm for animal cells. This technique has also been proposed in vivo to improve the efficacy of antitumour agents, such as bleomycin, in solid tumours in man (American U.S. Pat. No. 5,468,228, L. M. Mir). With pulses of very short duration (100 microseconds), these electrical conditions (800 to 1200 volts/cm) are very well suited to the intracellular transfer of small molecules. These conditions (pulses of 100 microseconds) have been applied with no improvement for the transfer of nucleic acids in vivo into the liver, where fields of less than 1000 volts/cm have proved completely ineffective, and even inhibitory compared with the injection of DNA in the absence of electrical impulses (Patent WO 97/07826 and Heller et al. FEBS Letters, 389, 225-8, 1996).

There are in fact difficulties with applying this technique in vivo because the administration of fields of such an intensity may cause extensive tissue lesions to a greater or lesser extent which do not represent a problem for the treatment of tumour tissues but which may have a major disadvantage for the healthy subject or the sick subject when the nucleic acid is administered into tissues other than tumour tissues, in particular into the striated muscle.

Whereas all the studies cited mention the need for high electric fields, of the order of 1000 volts/cm, to be effective in vivo, in a truly unexpected and remarkable manner, the applicants have now shown that the transfer of nucleic acids into muscles in vivo could be very substantially increased, without undesirable effects, by subjecting the muscle to electrical pulses of low intensity, for example 100 or 200 volts/cm and of a relatively long duration. Furthermore, the applicants have observed that the high variability in the expression of the transgene observed in the prior art for the transfer of DNA into the muscle was notably reduced by the method according to the invention.

Accordingly, the present invention relates to a method of transferring nucleic acids into one or more striated muscles in vivo, in which the muscle cells are brought into contact with the nucleic acid to be transferred, by direct administration into the tissue or by topical or systemic administration, and in which the transfer is brought about by application to the said muscles of one or more electrical pulses of an intensity between 1 and 800 volts/cm.

Preferably, the intensity of the field is between 4 and 400 volts/cm and the total duration of application is greater than 10 milliseconds. The number of pulses used is, for example, from 1 to 100,000 pulses and the frequency of the pulses is between 0.1 and 1000 Hertz. Preferably, the frequency of the pulses is between 0.2 and 100 Hertz. The pulses may also be delivered in an irregular manner and the function which describes the intensity of the field as a function of time may be variable. By way of example, the electric field delivered may result from the combination of at least one field having an intensity >400 V/cm and preferably between 500 and 800 volts/cm, with a short unit duration (<1 msec), followed by one or more pulses of lower intensity, for example <400 volts/cm, and preferably <200 volts/cm and with a longer unit duration (>1 msec). The integral of the function describing the variation of the electric field with time is greater than 1 kV×msec/cm. According to a preferred mode of the invention, this integral is greater than or equal to 5 kV×msec/cm.

According to a preferred mode of the invention, the field intensity of the pulses is between 30 and 300 volts/cm.

The electrical pulses are chosen from square wave pulses, electric fields generating exponentially decreasing waves, oscillating unipolar waves of limited duration, oscillating bipolar waves of limited duration, or other wave forms. According to a preferred mode of the invention, the electrical pulses are square wave pulses.

The administration of electrical pulses may be carried out by any method known to persons skilled in the art, for example:
- system of external electrodes placed on either side of the tissue to be treated, in particular non-invasive electrodes placed in contact with the skin,
- system of electrodes implanted in the tissues,
- system of electrodes/injector allowing the simultaneous administration of the nucleic acids and the electric field.

Within the framework of the present invention, the terms transfer of DNA or of nucleic acids by application of one or more electrical pulses, and the terms electrotransfer or alternatively electrotransfection should be considered to be equivalent and designate the transfer of nucleic acids or of DNA by application or in the presence of an electric field.

The administration being carried out in vivo, it is sometimes necessary to use intermediate products which provide electrical continuity with the non-invasive external electrodes. This may be for example an electrolyte in gel form.

The nucleic acids may be administered by any appropriate means, but are preferably injected in vivo directly into the muscle or administered by another route, local or systemic, which makes them available at the site of application of the electric field. The nucleic acids may be administered with agents allowing or facilitating transfer, as was mentioned above. In particular, these nucleic acids may be free in solution or combined with synthetic agents, or carried by viral vectors. The synthetic agents may be lipids or polymers known to a person skilled in the art, or alternatively targeting elements allowing attachment to the membrane of the target tissues. Among these elements, there may be mentioned vectors carrying sugars, peptides, antibodies or hormone receptors.

It can be understood, under these conditions of the invention, that the administration of the nucleic acids can precede, can be simultaneous with or can even be subsequent to the application of the electric fields.

Accordingly, the subject of the present invention is also a nucleic acid and an electric field of an intensity between 1 and 800 volts/cm, as combination product for their administration simultaneously, separately or spaced out over time, to the striated muscle in vivo. Preferably, the intensity of the field is between 4 and 400 volts/cm and, more preferably still, the intensity of the field is between 30 and 300 volts/cm.

The method according to the present invention can be used in gene therapy, that is to say therapy in which the expression of a transferred gene, but also the modulation or the blocking of a gene, makes it possible to provide the treatment of a particular pathological condition.

Preferably, the muscle cells are treated for the purpose of a gene therapy allowing:
- either the correction of dysfunctions of the muscle cells themselves (for example for the treatment of myopathies linked to genetic deficiencies),
- or the safeguard and/or the regeneration of the vascularization or the innervation of the muscle or of other muscles or organs by trophic, neurotrophic and angiogenic factors produced by the transgene,
- or the transformation of the muscle into an organ secreting products leading to a therapeutic effect such as the product of the gene itself (for example factors for regulation of thrombosis and of haemostasis, trophic factors, hormones such as insulin and the like) or such as an active metabolite synthesized in the muscle by virtue of the addition of the therapeutic gene,
- or a vaccine or immunostimulant application.

Another subject of the invention is the combination of the electrical pulses of a field with compositions containing nucleic acids formulated for any administration allowing access to a striated muscle by the topical, cutaneous, oral, vaginal, parenteral, intranasal, intravenous, intramuscular, subcutaneous, intraocular or transdermal route, and the like. Preferably, the pharmaceutical compositions of the invention contain a pharmaceutically acceptable vehicle for an injectable formulation, in particular for a direct injection into the desired organ, or for any other administration. They may be in particular isotonic sterile solutions or dry, in particular freeze-dried, compositions which, upon addition, depending on the case, of sterilized water or of physiological saline, allow the preparation of injectable solutions. The nucleic acid doses used for the injection as well as the number of administrations and the volume of injections may be adjusted according to various parameters, and in particular according to the mode of administration used, the relevant pathological condition, the gene to be expressed, or the desired duration of treatment.

The nucleic acids may be of synthetic or biosynthetic origin, or may be extracted from viruses or prokaryotic cells or from eukaryotic cells derived from unicellular organisms (for example yeasts) or from pluricellular organisms. They may be administered in combination with all or part of the components of the organism of origin and/or of the synthesis system.

The nucleic acid may be a deoxyribonucleic acid or a ribonucleic acid. It may be sequences of natural or artificial origin, and in particular genomic DNA, cDNA, mRNA, tRNA and rRNA, hybrid sequences or synthetic or semisynthetic sequences of modified or unmodified oligonucleotides. These nucleic acids may be obtained by any technique known to persons skilled in the art, and in particular by targeting libraries, by chemical synthesis or by mixed methods including chemical or enzymatic modification of sequences obtained by targeting libraries. They may be chemically modified.

In particular, the nucleic acid may be a DNA or a sense or antisense RNA or an RNA having catalytic property such as a ribozyme. "Antisense" is understood to mean a nucleic acid having a sequence complementary to a target sequence, for example an mRNA sequence the blocking of whose expression is sought by hybridization with the target sequence. "Sense" is understood to mean a nucleic acid having a sequence which is homologous or identical to a target sequence, for example a sequence which binds to a protein transcription factor and which is involved with the expression of a given gene. According to a preferred embodiment, the nucleic acid comprises a gene of interest and elements allowing the expression of the said gene of interest. Advantageously, the nucleic acid fragment is in the form of a plasmid.

The deoxyribonucleic acids may be single- or double-stranded, as well as short oligonucleotides or longer sequences. They may carry therapeutic genes, sequences for regulation of transcription or of replication, or regions for binding to other cellular components, and the like. For the purposes of the invention, "therapeutic gene" is understood to mean in particular any gene encoding an RNA or a protein product having a therapeutic effect. The protein product encoded may be a protein, a peptide and the like. This protein product may be homologous in relation to the target cell (that is to say a product which is normally expressed in the target cell when the latter exhibits no pathological condition). In this case, the expression of the transgene makes it possible, for example, to overcome an inadequate expression in the cell or the expression of an inactive or weakly active protein due to a modification, or makes it possible to overexpress the said protein. The therapeutic gene may also encode a mutant of a cellular protein having increased stability or a modified activity, and the like. The protein product may also be heterologous in relation to the target cell. In this case, an expressed protein may, for example, supplement or provide an activity which is deficient in the cell (treatment of myopathies or of enzymatic deficiencies), or may make it possible to combat a pathological condition, or to stimulate an immune response.

Among the therapeutic products for the purposes of the present invention, there may be mentioned more particularly the genes encoding enzymes such as α-1-antitrypsin, proteinase (metalloproteinases, urokinase, uPA, tPA, . . . streptokinase), proteases which cleave precursors to release active products (ACE, ICE, . . . ), or their antagonists (TIMP-1, tissue plasminogen activator inhibitor PAI, TFPI blood derivatives such as the factors involved in coagulation: factors VII, VIII, IX, complement factors, thrombin, hormones, or enzymes involved in the pathway for the synthesis of hormones, or factors involved in controlling the synthesis or the excretion or the secretion of hormones, such as insulin, factors related to insulin (IGF), or growth hormone, ACTH, enzymes for the synthesis of sex hormones, lymphokines and cytokines: interleukins, chemokines (CXC and CC), interferons, TNF, TGF, chemotactic factors or activators such as MIF, MAF, PAF, MCP-1, eotaxin, LIF and the like (French Patent No. 92 03120), growth factors, for example IGF, EGF, FGF, KGF, NGF, PDGF, PlGF, HGF, proliferin angiogenic factors such as VEGF or FGF, angiopoietin 1 or 2, endothelin enzymes for the synthesis of neurotransmitters, trophic, in particular neurotrophic, factors for the treatment of neurodegenerative diseases, of traumas which have damaged the nervous system, or of retinal degeneration, such as the members of the family of neurotrophins such as NGF, BDNF, NT3, NT4/5, NT6, their derivatives and related genes—members of the CNTF family such as CNTF, axokine, LIF and derivatives thereof—IL6 and its derivatives—cardiotrophin and its derivatives—GDNF and its derivatives—members of the family of IGFs, such as IGF-1, IGF-2 and derivatives thereof members of the FGF family, such as FGF 1, 2, 3, 4, 5, 6, 7, 8, 9 and derivatives thereof, TGFβ bone growth factors, haematopoietic factors such as erythropoietin, GM-CSF, M-CSF, LIF, and the like, proteins involved in cellular architecture such as dystrophin or a minidystrophin (French Patent No. 91 11947), suicide genes (thymidine kinase, cytosine deaminase, cytochrome P450-containing enzymes), genes for haemoglobin or other protein transporters, genes corresponding to the proteins involved in the metabolism of lipids, of the apolipoprotein type chosen from apolipoproteins A-I, A-II, A-IV, B, C-I, C-II, C-III, D, E, F, G, H, J and apo(a), metabolic enzymes such as for example lipases, lipoprotein lipase, hepatic lipase, lecithin-cholesterol acyltransferase, 7-alpha-cholesterol hydroxylase, phosphatidyl acid phosphatase, or lipid transfer proteins such as the cholesterol ester transfer protein and the phospholipid transfer protein, an HDL-binding protein or a receptor chosen, for example, from the LDL receptors, the remnant chylomicron receptors and the scavenger receptors, and the like. Leptin may furthermore be added to treat obesity, blood pressure regulating factors such as the enzymes involved in the metabolism of NO, angiotensin, bradykinin, vasopressin, ACE, renin, the enzymes encoding the mechanisms of synthesis and release of prostaglandins, thromboxane, adenosine, adenosine receptors, kallikreins and kallistatins, ANP, ANF, diuretic or antidiuretic factors, the factors involved in the synthesis, metabolism or release of mediators such as histamine, serotonin, cathecholamines, neuropeptides, anti-angiogenic factors such as the ligand for Tie-1 and for Tie-2, angiostatin, the ATF factor, plasminogen derivatives, endothelin, thrombospondins 1 and 2, PF-4, α- or β-interferon, interleukin-12, TNFα, urokinase receptor, flt1, KDR, PAI1, PAI2, TIMP1, prolactin fragment factors protecting against apoptosis, such as the AKT family, proteins capable of inducing cell death, which are either active by themselves such as caspases, or of the "prodrug" type which require activation by other factors, such as the proteins which activate pro-drugs into an agent causing cell death, such as the herpesvirus thymidine kinase, deaminases, which make it possible in particular to envisage anticancer therapies, proteins involved in intercellular contacts and adhesion: VCAM, PECAM, ELAM, ICAM, integrins, cathenins, proteins of the extracellular matrix, proteins involved in the migration of cells signal transduction type proteins of the type including FAK, MEKK, p38 kinase, tyrosin kinases, serine-threonine kinases, proteins involved in the regulation of the cell cycle (p21, p16, cyclins and the like) as well as the dominant-negative mutant or derived proteins which block the cell cycle and which can, where appropriate, induce apoptosis, transcription factors: jun, fos, AP1, p53 and the like and proteins of the p53 signalling cascade, cell structure proteins, such as the intermediate filaments (vimentin, desmin, keratins), dystrophin, the proteins involved in contractility and the control of muscle contractability, in particular the proteins involved in the metabolism of calcium and the calcium flows in the cells (SERCA and the like).

In the cases of proteins which function through ligand and receptor systems, it is possible to envisage using the ligand or the receptor (e.g. FGF-R, VEGF-R and the like). There may also be mentioned genes encoding fragments or mutants of ligand or receptor proteins, in particular proteins cited above, which exhibit either an activity which is higher than the full-length protein, or an antagonist activity, or even of the "dominant-negative" type relative to the initial protein (for example receptor fragments inhibiting the availability of circulating proteins, associated or otherwise with sequences inducing secretion of these fragments relative to anchorage in the cell membrane, or other systems for modifying intracellular traffic in these ligand-receptor systems so as to divert the availability of one of the elements) or even possessing an inherent activity distinct from that of the total protein (e.g. ATF).

Among the other proteins or peptides which may be secreted by the muscle, it is important to underline antibodies, the variable fragments of single-chain antibody (ScFv) or any other antibody fragment possessing recognition capacities for its use in immunotherapy, for example for the treatment of infectious diseases, of tumours, of autoimmune diseases such as multiple sclerosis (antiidiotype antibodies), as well as ScFv's which bind to proinflammatory cytokines such as, for example, IL1 and TNFα for the treatment of rhumatoid arthritis. Other proteins of interest are, in a nonlimiting manner, soluble receptors such as, for example, the soluble CD4 receptor or the soluble receptor for TNF for anti-HIV therapy, the TNFα receptor or the soluble receptor IL1 for the treatment of rhumatoid arthritis, the soluble receptor for acetylcholine for the treatment of myasthenia; substrate peptides or enzyme inhibitors, or peptides which are agonists or antagonists of receptors or of adhesion proteins such as, for example, for the treatment of asthma, thrombosis, restenosis, metastases or inflammation; artificial, chimeric or truncated proteins. Among the hormones of essential interest, there may be mentioned insulin in the case of diabetes, growth hormone and calcitonin. There may also be mentioned proteins capable of inducing an antitumour immunity or stimulating the immune response (IL2, GM-CSF, IL12 and the like). Finally, there may be mentioned cytokines which reduce the $T_{H1}$ response such as IL10, IL4 and IL13.

The numerous examples which precede and those which follow illustrate the potential scope of the field of application of the present invention.

The therapeutic nucleic acid may also be an antisense sequence or gene whose expression in the target cell makes it possible to control the expression of genes or the transcription of cellular mRNAs. Such sequences may, for example, be transcribed in the target cell into RNA complementary to cellular mRNAs and thus block their translation into protein, according to the technique described in European Patent No. 140 308. The therapeutic genes also comprise the sequences encoding ribozymes, which are capable of selectively destroying target RNAs (European Patent No. 321 201).

As indicated above, the nucleic acid may also comprise one or more genes encoding an antigenic peptide capable of generating an immune response in humans or in animals. In this particular embodiment, the invention therefore allows either the production of vaccines, or the carrying out of immunotherapeutic treatments applied to humans or to animals, in particular against microorganisms, viruses or cancers. It may be in particular antigenic peptides specific for the Epstein-Barr virus, the HIV virus, the hepatitis B virus (European Patent No. 185 573), the pseudo-rabies virus, the "syncytia forming virus", other viruses or antigens specific for tumours such as the MAGE proteins (European Patent No. 259 212), such as the MAGE 1 or MAGE 2 proteins, or antigens which can stimulate an antitumour response such as bacterial heat shock proteins.

Preferably, the nucleic acid also comprises sequences allowing and/or promoting the expression, in the muscle, of the therapeutic gene and/or of the gene encoding the antigenic peptide. They may be sequences which are naturally responsible for the expression of the gene considered when these sequences are capable of functioning in the transfected cell. They may also be sequences of different origin (responsible for the expression of other proteins, or even synthetic). In particular, they may be promoter sequences of eukaryotic or viral genes. For example, they may be promoter sequences derived from the genome of the cell which it is desired to transfect. Among the eukaryotic promoters, there may be used any promoter or derived sequence stimulating or repressing the transcription of a gene in a specific or nonspecific, strong or weak manner. They may be in particular ubiquitous promoters (HPRT, vimentin, α-actin, tubulin and the like), promoters of therapeutic genes (MDR or CTFR type and the like), tissue-specific promoters (of the type including promoters of the genes for desmin, myosins, creatine kinase, phosphoglycerate kinase) or alternatively promoters responding to a stimulus such as promoters responding to natural hormones (receptor for steroid hormones, receptor for retinoic acid and the like) or a promoter regulated by antibiotics (tetracyclin, rapamycin and the like), promoters responding to a diet such as the promoters responding to fibrates, or other promoters responding to other molecules of natural or synthetic origin. Likewise, they may be promoter sequences derived from the genome of a virus. In this regard, there may be mentioned, for example, the promoters of the adenovirus EIA or MLP genes or promoters derived from the genomes of the CMV, RSV and SV40 viruses, and the like. The promoters may be inducible or repressible. In addition, these expression sequences may be modified by the addition of activating or regulatory sequences, allowing a conditional or transient expression or a tissue-specific or predominant expression, and the like.

Moreover, the nucleic acid may also comprise, in particular upstream of the therapeutic gene, a signal sequence directing the therapeutic product synthesized in the secretory pathways of the target cell. This signal sequence may be the natural signal sequence of the therapeutic product, but it may also be any other functional signal sequence, or an artificial signal sequence. The nucleic acid may also comprise a signal sequence directing the synthesized therapeutic product towards a particular compartment of the cell, such as, for example, peroxisomes, lysosomes and mitochondria for the treatment, for example, of mitochondrial genetic diseases.

Other genes which are of interest have been described in particular by McKusick, V. A. Mendelian (Inheritance in man, catalogs of autosomal dominant, autosomal recessive, and X-linked phenotypes. Eighth edition, John Hopkins University Press (1988)), and in Stanbury, J. B. et al. (The metabolic basis of inherited disease, Fifth edition, McGraw-Hill (1983)). The genes of interest cover the proteins involved in the metabolism of amino acids, lipids and other constituents of the cell.

There may thus be mentioned, with no limitation being implied, the genes associated with diseases of carbohydrate metabolism such as for example fructose-1-phosphate aldolase, fructose-1,6-diphosphatase, glucose-6-phosphatase, lysosomal α-1,4-glucosidase, amylo-1,6-glucosidase, amylo-(1,4:1,6)-transglucosidase, muscle phosphorylase, muscle phosphofructokinase, phosphorylase-β-kinase, galactose-1-phosphate uridyl transferase, all the enzymes of the complex pyruvate dehydrogenase, pyruvate carboxylase, 2-oxoglutarate glyoxylase carboxylase, D-glycerate dehydrogenase.

There may also be mentioned:
the genes associated with diseases of amino acid metabolism such as for example phenylalanine hydroxylase, dihydrobiopterin synthetase, tyrosine aminotransferase, tyrosinase, histidinase, fumarylacetoacetase, glutathione synthetase, γ-glutamylcysteine synthetase, ornithine-δ-aminotransferase, carbamoylphosphate synthetase, ornithine carbamoyltransferase, argininosuccinate synthetase, argininosuccinate lyase, arginase, L-lysine dehydrogenase, L-lysine ketoglutarate reductase, valine transaminase, leucine isoleucine transaminase, decarboxylase for the branched-chain 2-keto acids, isovaleryl-CoA dehydrogenase, acyl-CoA dehydrogenase, 3-hydroxy-3-methylglutaryl-CoA lyase, acetoacetyl-CoA 3-ketothiolase, propionyl-CoA carboxylase, methylmalonyl-CoA mutase, ATP:cobalamine adenosyltransferase, dihydrofolate reductase, methylenetetrahydrofolate reductase, cystathionine β-synthetase, the sarcosine dehydrogenase complex, proteins belonging to the system for cleaving glycine, β-alanine transaminase, serum carnosinase, cerebral homocarnosinase;

the genes associated with diseases of fat and fatty acid metabolism, such as for example lipoprotein lipase, apolipoprotein C-II, apolipoprotein E, other apolipoproteins, lecithin-cholesterol acyltransferase, LDL receptor, liver sterol hydroxylase, "phytanic acid" α-hydroxylase;

the genes associated with lysosomal deficiencies, such as for example lysosomal α-L-iduronidase, lysosomal iduronate sulphatase, lysosomal heparan N-sulphatase, lysosomal N-acetayl-α-D-glucosamimidase, lysosomal acetyl-CoA:α-glucosamine N-acetyltransferase, lysosomal N-acetyl-α-D-glucosamine 6-sulphatase, lysosomal galactosamine 6-sulphate sulphatase, lysosomal β-galactosidase, lysosomal arylsulphatase B, lysosomal β-glucuronidase, N-acetylglucosaminyl-phosphotransferase, lysosomal α-D-mannosidase, lysosomal α-neuramimidase, lysosomal aspartylglycosamimidase, lysosomal α-L-fucosidase, lysosomal acid lipase, lysosomal acid ceramidase, lysosomal sphingomyelinase, lysosomal glucocerebrosidase and lysosomal galactocerebrosidase, lysosomal galactosylceramidase, lysosomal arylsulphatase A, α-galactosidase A, lysosomal acid β-galactosidase, α chain of lysosomal hexoamimidase A.

There may also be mentioned, in a nonrestrictive manner, the genes associated with diseases of steroid and lipid metabolism, the genes associated with diseases of purine and pyrimidine metabolism, the genes associated with diseases of porphyrin and haem metabolism, the genes associated with diseases of connective tissue, s and bone metabolism as well as the genes associated with blood diseases and diseases of the haematopoietic organs, muscle diseases (myopathy), diseases of the nervous system (neurodegenerative diseases) or diseases of the circulatory apparatus (treatment of ischaemias and of stenosis for example) and the genes involved in mitochondrial genetic diseases.

In the method according to the invention, the nucleic acid may be combined with any type of vector or any combination of these vectors which make it possible to improve the transfer of genes, for example, in a nonlimiting manner, with vectors such as viruses, synthetic or biosynthetic agents (for example lipid, polypeptide, glycosidic or polymeric agents), or beads which are propelled or otherwise. The nucleic acids may also be injected into a muscle which has been subjected to a treatment intended to improve the transfer of genes, for example a treatment of a pharmacological nature by local or systemic application, or an enzymatic, permeabilizing (use of surfactants), surgical, mechanical, thermal or physical treatment.

The advantage of the use of the muscle in gene therapy lies in numerous factors:
the remarkable stability of the expression of the transgenes, more than several months, and therefore allowing the stable and sustained production of an intramuscular or secreted therapeutic protein,
the ease of access to the muscle tissue, allowing a direct, rapid and non-dangerous administration into a non-vital organ,
the large volume of the muscle mass, allowing multiple sites of administration,
widely demonstrated secretory capacity of the muscle.

To these advantages, there may be added the safety provided by the local treatment linked to the use of local and targeted electric fields.

By virtue of all these advantages and the safety linked to the use of weak fields, the present invention could be applied in the region of the cardiac muscle for the treatment of cardiopathies, for example using a suitable defibrillator. It could also be applied to the treatment of restenosis by the expression of genes inhibiting the proliferation of the smooth muscle cells such as the GAX protein.

The combination of fields which are not very intense and which are administered over a long period, applied in particular to the muscles in vivo, improves the transfection of nucleic acids without causing notable damage to the tissues. These results improve the yield of DNA transfers within the context of gene therapy using nucleic acids.

Consequently, the advantages of the muscle tissue combined with the method according to the invention make it possible, for the first time, to envisage producing, by gene therapy, an agent at physiological and/or therapeutic doses, either in the muscle cells, or secreted in their vicinity or into the blood stream or the lymph circulation. Furthermore, the method according to the invention allows, for the first time, fine modulation and control of the effective quantity of transgene expressed by the possibility of modulating the volume of muscle tissue to be transfected, for example with multiple sites of administration, or the possibility of modulating the number, the shape, the surface and the arrangement of the electrodes. An additional element of control comes from the possibility of modulating the efficiency of transfection by varying the field intensity, the number, the duration and the frequency of the pulses, and obviously according to the state of the art, the quantity and the volume of nucleic acids to be administered. It is thus possible to obtain an appropriate transfection level at the desired production or secretion level. The method finally allows increased safety compared with the chemical or viral methods for transferring genes in vivo, for which the affecting of organs other than the target organ cannot be completely excluded or controlled. Indeed, the method according to the invention allows control of the localization of the transfected tissues (strictly linked to the volume of tissue subjected to the local electrical pulses) and therefore provides the possibility of a return to the initial situation by complete or partial removal of the muscle, which is made possible by the non-vital character of this tissue and by its regeneration capacities. This great flexibility of use makes it possible to optimize the method according to the animal species (human and veterinary applications), the age of the subject, his physiological and/or pathological condition.

The method according to the invention makes it possible, in addition, for the first time, to transfect nucleic acids of large size unlike the viral methods which are limited by the size of the capsid. This possibility is essential for the transfer of genes of a very large size such as that for dystrophin or genes with introns and/or regulatory elements of large size, which is necessary for example for a physiologically regulated production of hormones. This possibility is essential for the transfer of episomes or of yeast artificial chromosomes or of minichromosomes.

The following examples are intended to illustrate the invention in a nonlimiting manner.

In these examples, reference will be made to the following figures:

FIG. 1: effects of electrical pulses of high field intensity on the transfection of plasmid DNA pXL2774 into the cranial tibial muscle in mice; mean values ±SEM, FIG. 2: effects of electrical pulses of intermediate field intensity on the transfection of plasmid DNA pXL2774 into the cranial tibial muscle in mice; mean values ±SEM, FIG. 3: effects of electrical pulses of low field intensity and of different durations on the transfection of plasmid DNA pXL2774 into the cranial tibial muscle in mice; mean values ±SEM, FIG. 4: effects of electrical pulses of low field intensity and of different durations on the transfection of plasmid DNA pXL2774 into the cranial tibial muscle in mice; mean values ±SEM, FIG. 5: efficiency of electrotransfection of plasmid DNA pXL2774 into the cranial tibial muscle of mice at low electric field intensities: mean values ±SEM.

Figure 6:
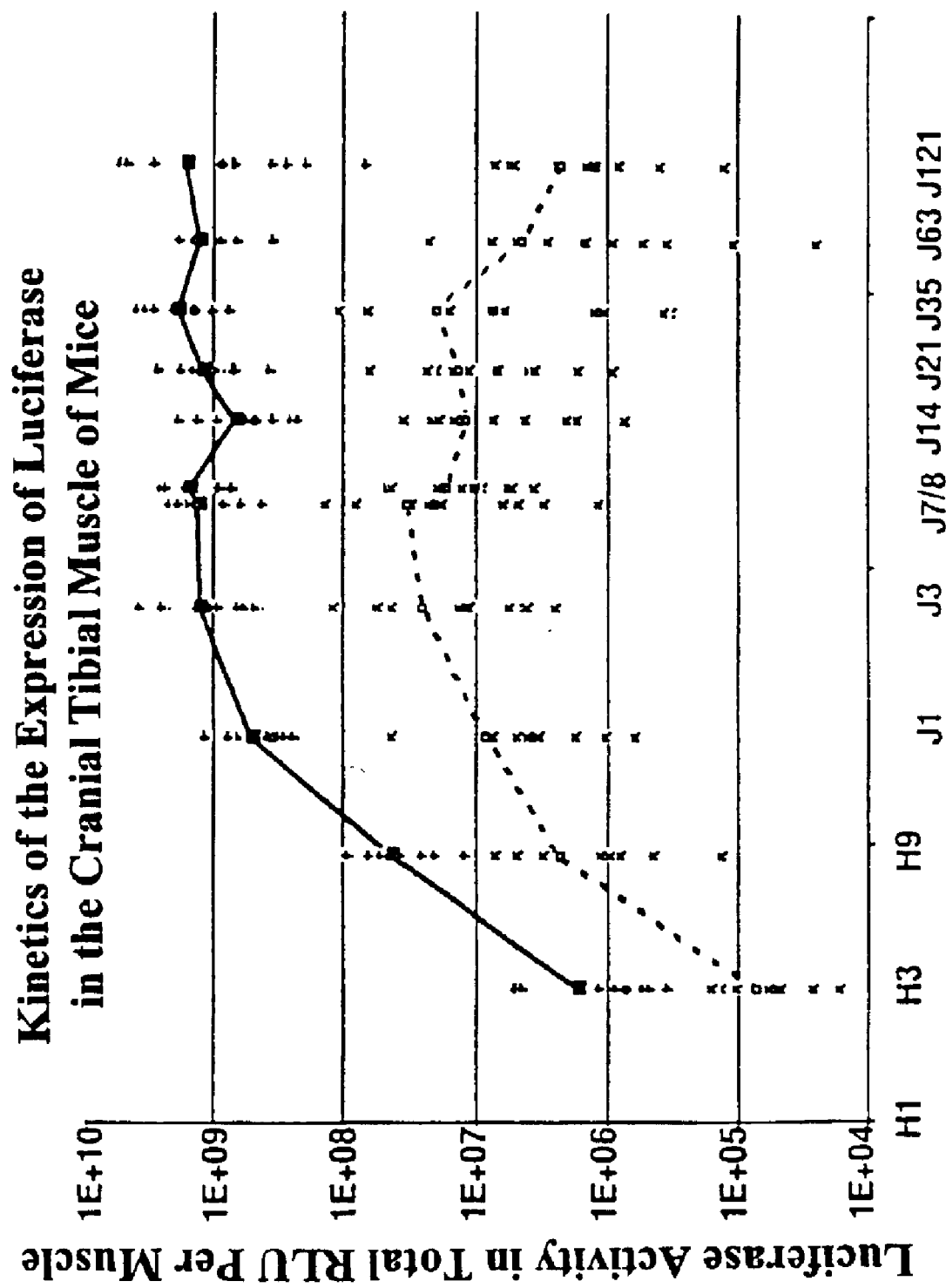

FIG. 6: kinetics of expression of luciferase in mouse cranial tibial muscle. Administration of the plasmid pXL2774 with electrotransfer (■) and without electrotransfer (X); mean values ±SEM.

Figure 7:
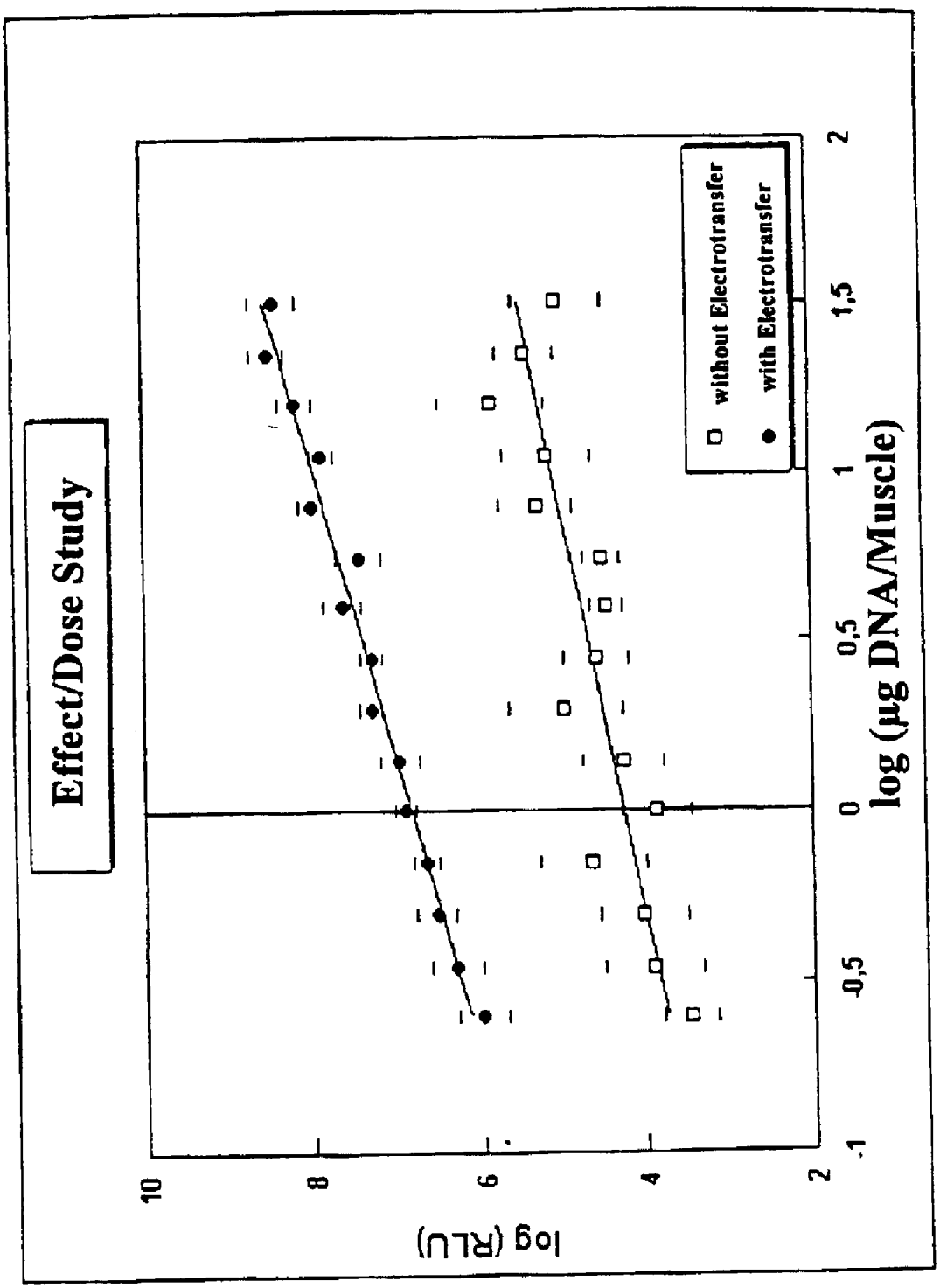

FIG. 7: level of expression of the transgene as a function of the administered DNA dose, with electrotransfer (●) and without electrotransfer (□).

Figure 8:
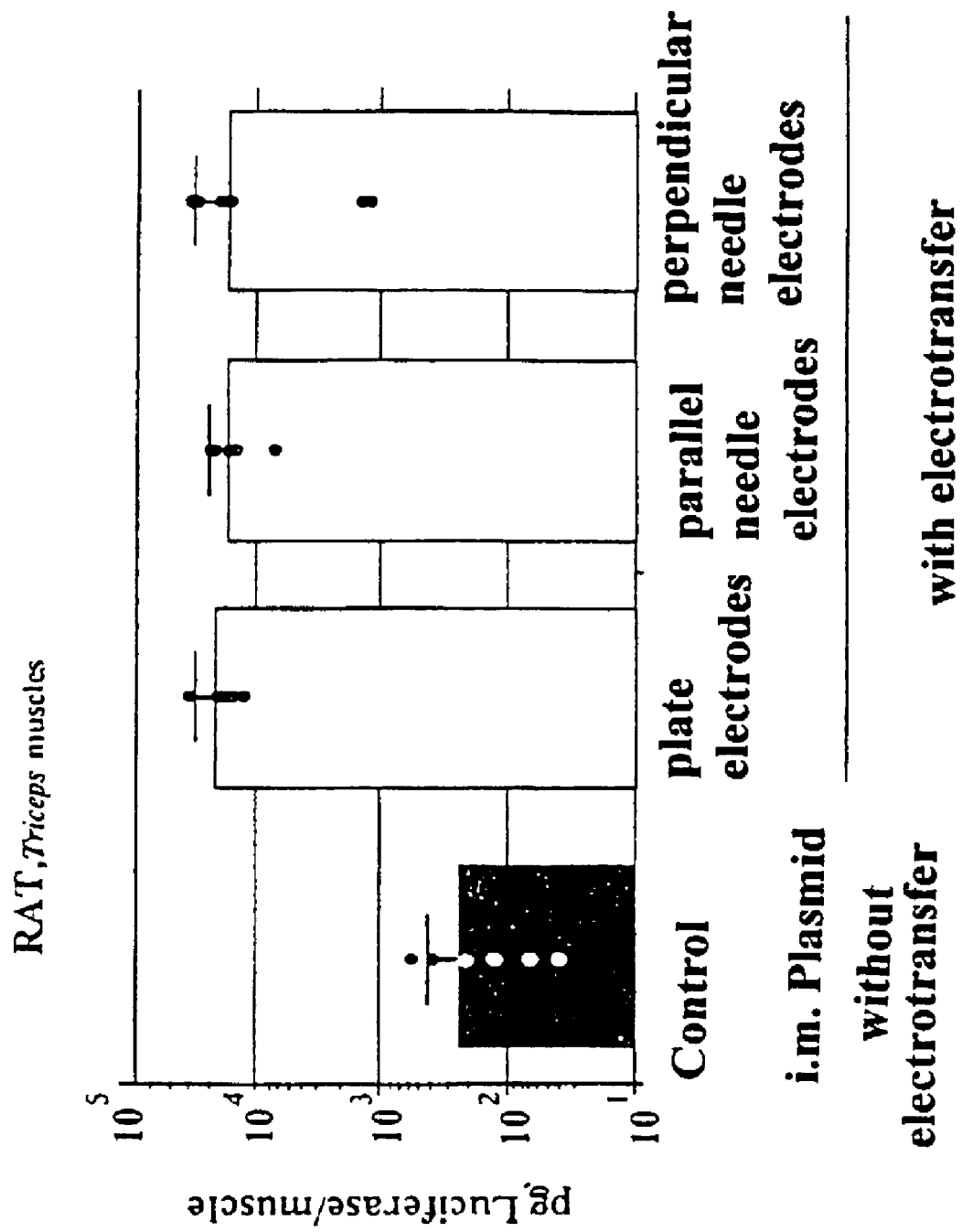

FIG. 8: effect of various types of electrodes on the efficiency of the electrotransfer.

Figure 9:
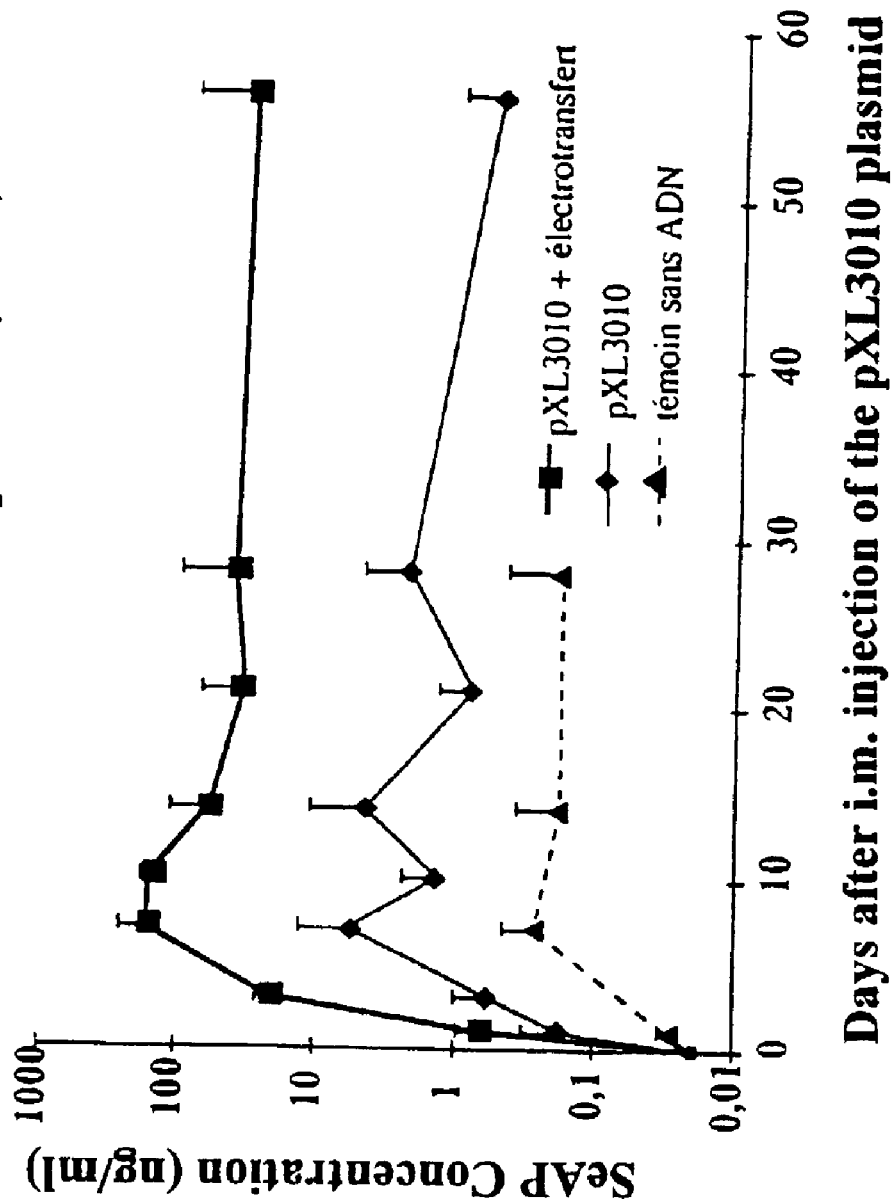

FIG. 9: kinetics of the serum concentration of secreted alkaline phosphatase. Administration of the plasmid pXL3010 with electrotransfer (■) and without electrotransfer (♦); mean values ±SEM.

Figure 10:
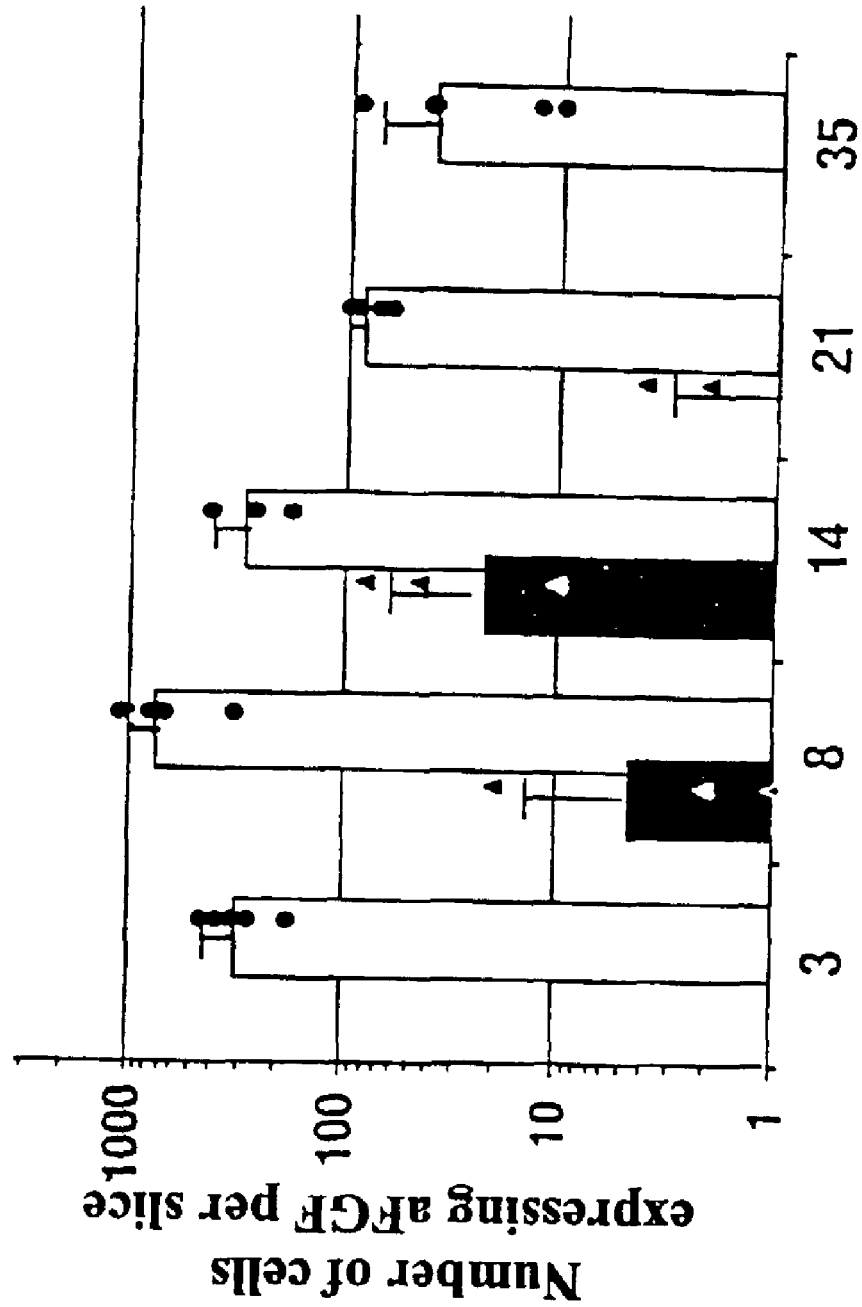

FIG. 10: kinetics of expression of FGF1 in the muscle with electrotransfer (white histogram bars), and without electrotransfer (black histogram bars).

Figure 13:
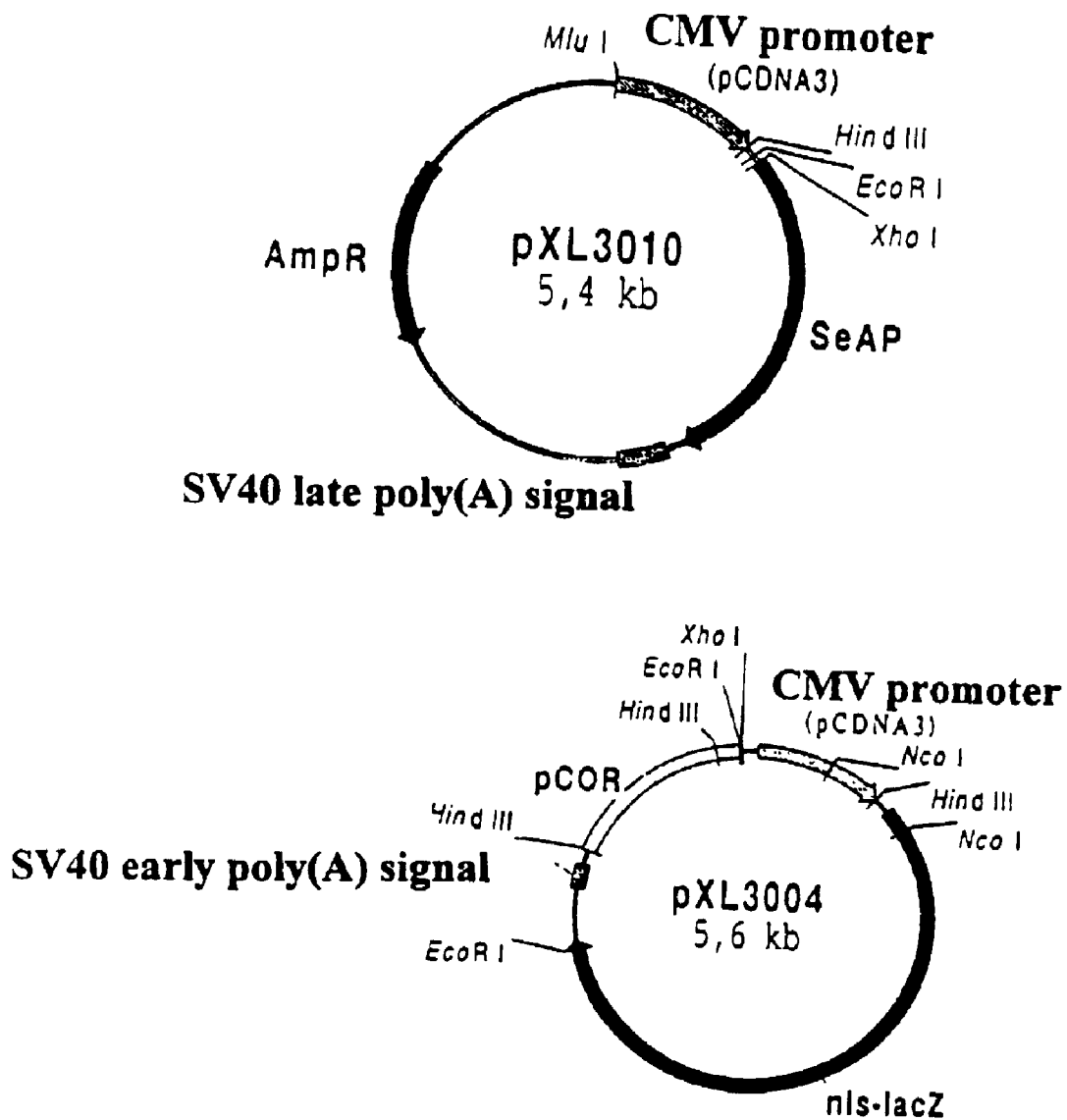
Figure 16:
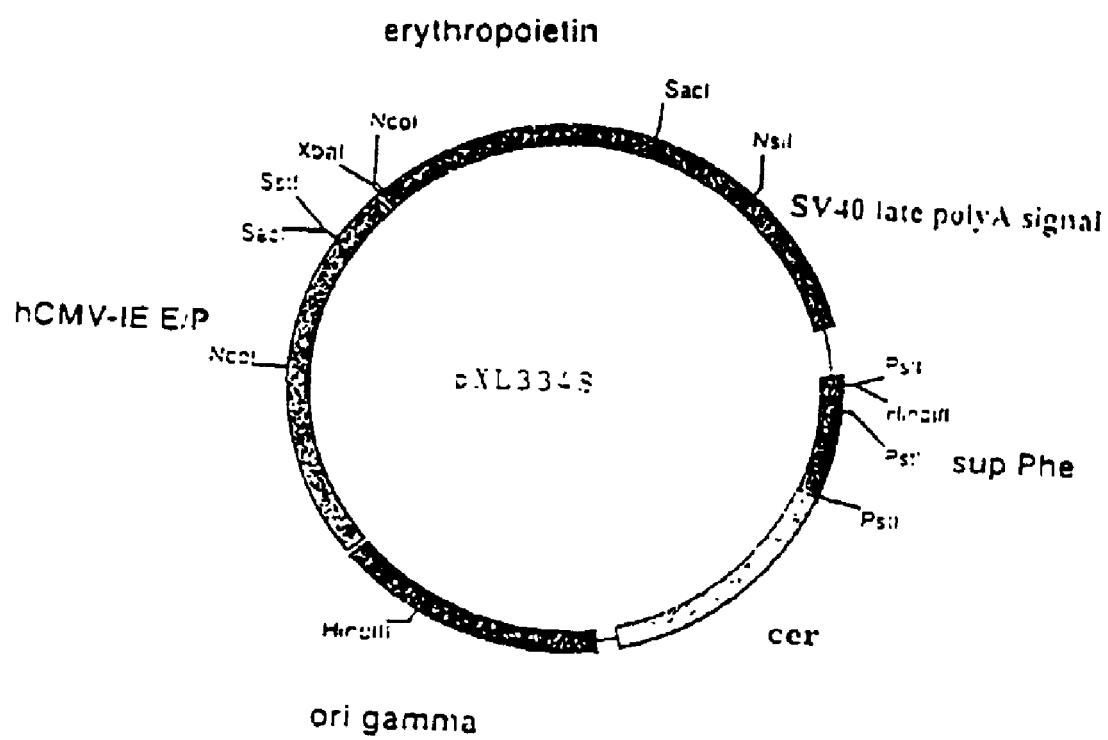

FIG. 11: maps of the plasmids pXL3179 and pXL3212.
FIG. 12: maps of the plasmids pXL3388 and pXL3031.
FIG. 13: maps of the plasmids pXL3004 and pXL3010.
FIG. 14: maps of the plasmids pXL3149 and pXL3096.
FIG. 15: maps of the plasmids pXL3353 and pXL3354.
FIG. 16: map of the plasmid pXL3348.

EXAMPLE 1

Experiment Carried Out Under the Conditions of the Prior State of the Art in which the Electric Fields Prove to be Inhibitors of Transfection Standard electroporation conditions, such as those used in the prior art and which have been discussed above, were tested and proved to be ineffective or to even have an inhibitory action on the transfer of nucleic acids (plasmid DNA) in the striated muscle.

Materials and Methods—General Operating Conditions

In this example, the following products were used:

DNA pXL2774 (Patent PCT/FR 96/01414) is a plasmid DNA comprising the reporter gene for luciferase. Other products are available from commercial suppliers: Ketamine, Xylazine, physiological saline (0.9% NaCl).

An oscilloscope and a commercial generator of (rectangular or square) electrical pulses (electro-pulsator PS 15, Jouan, France) were used. The electrodes used are flat stainless steel electrodes 1 to 15 mm apart.

The experiment is carried out on the mouse C57 B1/6. Mice from different cages are randomly separated before the experiment ("randomization").

The mice are anaesthetized with a ketamine and xylazine mixture. The plasmid solution (30 $\mu$l of a solution at 500 $\mu$g/ml of 0.9% NaCl) is injected longitudinally through the skin into the cranial tibial muscle of the left and right legs with the aid of a Hamilton syringe. The two electrodes are coated with a conducting gel and the injected leg is placed between the electrodes in contact with them.

The electrical pulses are applied perpendicularly to the axis of the muscle with the aid of a generator of square pulses one minute after the injection. An oscilloscope makes it possible to control the intensity in volts (the values indicated in the examples represent the maximal values), the duration in milliseconds and the frequency in hertz of the pulses delivered, which is 1 Hz. 8 consecutive pulses are delivered.

To evaluate the transfection of the muscle, the mice are humanely killed 7 days after the administration of the plasmid. The cranial tibial muscles of the left and right legs are then removed, weighed, placed in lysis buffer and ground. The suspension obtained is centrifuged in order to obtain a clear supernatant. The measurement of the luciferase activity is carried out on 10 μl of supernatant with the aid of a commercial luminometer in which the substrate is added automatically to the solution. The intensity of the luminescent reaction is given in RLU (Relative Luminescence Unit) for a muscle knowing the total volume of suspension ($1 \times 10^6$ RLU are equivalent to 30 pg of luciferase). Each experimental condition is tested on 10 points: 5 animals injected bilaterally. Statistical comparisons are carried out with the aid of non-parametric tests.

Results and Discussion

Two figures, of which the scale is linear or logarithmic, illustrate the results.

In this first experiment, the effects of an electric field of 800 to 1200 volts/cm which allows electroporation of tumours (Mir et al. Eur. J. Cancer 27, 68, 1991) were tested.

It is observed, according to FIG. 1, that relative to the control group, where the DNA is injected without an electrical pulse:

with 8 pulses of 1200 volts/cm and of a duration of 0.1 msec, the mean value of the luciferase activity is much lower, with pulses of 1200 volts/cm and of 1 msec, 3 animals are dead, the mean value of the luciferase activity is much lower, with pulses of 800 volts/cm and of 1 msec, the mean value of the luciferase activity is also significantly reduced.

Most of the muscles which were subjected to the action of the electric field are visibly impaired (friable and of a whitish appearance).

EXAMPLE 2

Experiment for Electrotransfer of Nucleic Acids at Moderate Electric Fields

This experiment is carried out with C57 B1/6 mice. Apart from the electric field intensity of the pulses and their duration, the practical conditions are those of Example 1.

The results are shown in FIG. 2. The result of Example 1 is reproduced, that is to say the inhibitory effect of a series of 8 pulses at 800 volts/cm of a duration of 1 msec on the luciferase activity detected in the muscle. With a field of 600 volts/cm, the same inhibition and the same impairment of the muscle tissue are observed. On the other hand, in a remarkable and surprising manner, the decrease in voltage makes it possible to no longer visibly impair the muscles and, furthermore, at 400 and 200 volts/cm, the level of transfection of the muscles is on average greater than that obtained on the muscles not subjected to a field. It should be noted that, relative to the control group (not subjected to an electric field), the dispersion of the luciferase activity values is reduced at 200 volts/cm (SEM=20.59% of the mean value against 43.32% in the absence of electric field (FIG. 2A)).

EXAMPLE 3

Experiment for Electrotransfer of Nucleic Acids with Pulses of Low Field Intensity Showing a Very High Stimulation of the Expression of the Transgene This experiment is carried out with C57 B1/6 mice. Apart from the electric field intensity of the pulses and their duration, and the fact that the pulses are delivered 25 seconds after the injection of the DNA, the practical conditions are those of the preceding examples.

The results are shown in FIG. 3. The mean value of the expression of the luciferase transgene is markedly increased with a pulse duration of 20 msec at 100 volts/cm, and from a pulse duration of 5 msec at 200 volts/cm.

This experiment also clearly shows that the mean value of the luciferase activity obtained by electrotransfection of the DNA into the muscle is a function of the duration of the electrical pulses, when voltages of 200 and 100 volts/cm are used. It is also observed that the dispersion of the values is notably reduced for the electrotransfected muscle groups (FIG. 3A). In the absence of electrical pulses (control), the SEM represents 77.43% of the mean value whereas the relative SEM of the mean is reduced to 14% (200 volts/cm, 5 msec), 41.27% (200 volts/cm, 20 msec) and between 30% and 48% for the electrotransfer at 100 volts/cm of electric field.

Under the best condition for this experiment, the expression of the transgene is improved by a factor of 89.7 compared with the control injected in the absence of electrical pulses.

EXAMPLE 4

Experiment for Electrotransfer of Nucleic Acids into the Muscle at 200 Volts/cm Showing an Increase in the Expression of the Transgene by a Factor Greater than 200

This experiment is carried out in DBA 2 mice, with electrical pulses of a field intensity of 200 volts/cm and of variable duration, the other conditions of this experiment being those of Example 3.

This example confirms that at 200 volts/cm, the transfection of the luciferase activity is increased from a pulse duration of 5 msec and then continues to increase for longer durations (FIGS. 4 and 5). Here again, a reduction in the inter-individual variability indicated by the SEM relative to the non-electrotransfected control (the relative value of the SEM is equal to 35% for the control and 25, 22, 16, 18, 16 and 26% for series of pulses of 1, 5, 10, 15, 20 and 24 msec respectively), is observed with electrotransfection.

Under the best condition for this experiment, the expression of the transgene is improved by a factor of 205 relative to the control injected in the absence of electrical pulses. It thus appears that the variation of the duration of each pulse delivered is a means of modulating the efficiency of the transfer of nucleic acids and of adjusting the level of expression of the transgene.

EXAMPLE 5

Efficiency of the Electrotransfer of Nucleic Acids as a Function of the Product "Number of Pulses×Field Intensity×Duration of Each Pulse"

FIG. 5 exemplifies the importance of the parameter corresponding to the product "number of pulses×field intensity×duration of each pulse". This parameter in fact corresponds to the integral, as a function of time, of the function which describes the variation of the electric field.

The representation in FIG. 5 of the results obtained during experiments 2, 3 and 4 with electric field intensities of 200 V/cm, 100 V/cm or in the absence of electric fields shows that the transfection efficiency increases as a function of the product of the total duration of exposure to the electric field by the field intensity. A stimulating effect is obtained for a value greater than 1 kV×msec/cm of the product "electric field×total duration of the pulses". According to a preferred mode, a stimulation is obtained for a value greater than or equal to 5 kV×msec/cm of the product "electric field×total duration of the pulses".

EXAMPLE 6

Effect of the Increase in the Duration of the Electrical Pulses

This example illustrates that it is possible to increase the unit duration of the pulses well above the values tested in Example 4.

This experiment is carried out with C57B1/6 mice. The plasmid used is the plasmid pXL2774, the quantity of DNA administered is 15 μg. The electropulsator used to deliver the electrical pulses of a duration greater than 20 msec is a commercial electropulsator (Genetronics, model T 820, USA, San Diego, Calif.). The electrical pulses are variable in number and duration but have a constant field intensity of 200 volts/cm; the other conditions for this experiment are those described in Example 1. The results are presented in Table 1.

TABLE 2

Mean values +/- SEM of the luciferase activity in millions of RLU per muscle. N = 10 per group. Conditions: field intensity 200 V/cm, variable number of pulses of 20 msec, frequency 1 Hz.

| Pulse number | 0 | 1 | 2 | 4 | 6 | 8 | 12 | 16 |
|---|---|---|---|---|---|---|---|---|
| Total RLU | 70 ± 56 | 147 ± 26 | 281 ± 46 | 439 ± 50 | 678 ± 129 | 819 ± 73 | 929 ± 169 | 890 ± 137 |

It is observed that the expression of luciferase increases substantially from the application of a single pulse, and that it continues to increase as a function of the number of pulses. It thus appears that the variation in the number of pulses delivered is a means of modulating the efficiency of the transfer of nucleic acids and of adjusting the level of expression of the transgene.

A reduction in the variability of the response demonstrated by the reduction in the value of the SEM is also

TABLE 1

Mean values +/- SEM of the luciferase activity in millions of RLU per muscle. N = 10 for each group.
Electrotransfer conditions: field intensity 200 V/cm, 8 or 4 pulses (variable unit duration), frequency 1 Hz.

| Pulse duration (msec) | 0 | 1 | 5 | 10 | 20 | 30 | 40 | 50 | 60 | 80 |
|---|---|---|---|---|---|---|---|---|---|---|
| Experiment A 8 pulses | 11 ± 5 | 39 ± 6 | 211 ± 26 | 288 ± 46 | 1158 ± 238 | 1487 ± 421 | 2386 ± 278 | | | |
| Experiment A 4 pulses | 11 ± 5 | 26.8 ± 6 | 123 ± 17 | 246 ± 32 | 575 ± 88 | 704 ± 130 | | 3440 ± 1077 | | |
| Experiment B 4 pulses | 15 ± 8 | | | | | | | 2885 ± 644 | 2626 ± 441 | 1258 ± 309 |

An increase in the expression of the transgene is observed with the extension of the unit duration of the pulses (at least up to 40 msec for a series of 8 pulses and at least up to 50 msec for a series of 4 pulses of 200 volts/cm intensity). This example shows that the optimum of the duration of the pulses depends on the number of pulses used and that the unit duration of the pulses may be up to at least 80 msec, this value of duration not being limiting.

EXAMPLE 7

Efficiency of the Electrotransfer as a Function of the Number of Electrical Pulses This example demonstrates the effect of increasing the number of electrical pulses on the efficiency of the transfer of nucleic acids.

This experiment is carried out with C57B1/6 mice. The plasmid used is the plasmid pXL2774, the quantity of DNA administered is 15 μg. The electrical pulses are variable in number. The duration of each pulse is 20 msec. The field intensity is 200 volts/cm. The other conditions for this experiment are those described in Example 1. The results are presented in Table 2.

confirmed relative to the mean for all the groups subjected to the electrotransfer.

EXAMPLE 8

Effect of the Increase in the Frequency of the Electrical Pulses

This example shows that the increase in the frequency of the pulses makes it possible, unexpectedly, to enhance the efficiency of the transfection. Moreover and in a clinical perspective, the increase in the frequency should improve the patient's comfort by reducing the total duration of the treatment.

This experiment is carried out with C57B1/6 mice. The plasmid used is the plasmid pXL2774, the quantity of DNA administered is 15 μg. The frequency of the electrical pulses is variable (from 0.1 to 4 Hertz). The duration of each pulse is 20 msec, the field intensity is 200 volts/cm, the other conditions of this experiment are those described in Example 1. The results are presented in Table 3.

TABLE 3

Mean values +/− SEM of the luciferase activity in millions of RLU per muscle. N = 10 for each group.
Conditions: field intensity 200 V/cm, 8 or 4 pulses of 20 msec, variable frequency.

| Frequency Hertz | 0 | 0.1 | 0.2 | 0.5 | 1 | 2 | 3 | 4 |
|---|---|---|---|---|---|---|---|---|
| Experiment A 8 pulses | 5 ± 2 | 54 ± 13 | 95 ± 16 | 405 ± 60 | 996 ± 156 | 1528 ± 257 | | |
| Experiment A 4 pulses | | 114 ± 14 | 163 ± 24 | 175 ± 26 | 337 ± 53 | 587 ± 90 | | |
| Experiment B 8 pulses | 21 ± 14 | | | | 1294 ± 189 | 2141 ± 387 | 3634 ± 868 | 2819 ± 493 |
| Experiment B 4 pulses | | | | | 1451 ± 228 | 1572 ± 320 | 1222 ± 126 | 2474 ± 646 |

The results obtained in experiment "A", Table 3, show that the higher frequencies (≧1 Hz) are more effective than the low frequencies which correspond to a longer duration between two consecutive pulses (10 seconds at 0.1 Hertz). The transfection efficiency increases with the frequency over the range of values tested from 0.1 to 4 Hertz for 4 pulses and from 0.1 to 3 Hertz for 8 pulses.

EXAMPLE 9

Effect of the Application of an Electric Field Varying According to a Decreasing Exponential as a Function of Time This example demonstrates the effect of the application of an electric field varying according to a decreasing exponential on the efficiency of the transfer of nucleic acids.

This experiment is carried out with C57B1/6 mice.

The plasmid used is the plasmid pXL3031. The plasmid pXL3031 (FIG. 12) is a vector derived from the plasmid pXL2774 (WO97/10343) into which the luc+gene encoding modified *Photinus pyralis* luciferase (cytoplasmic) obtained from pGL3basic (Genbank: CVU47295) has been introduced under the control of the promoter obtained from the human cytomegalovirus early region (hCMV IE, Genbank HS51EE) and of the polyadenylation signal of the SV40 virus late region (Genbank SV4CG). The quantity of DNA administered is 10 μg.

The generator of electrical pulses used makes it possible to deliver pulses with an electric field intensity varying according to a decreasing exponential as a function of time (Equibio electropulsator, easyject T plus model, Kent, UK). The voltage imposed is the voltage at the exponential peak. The second adjustable parameter is the capacitance (μFarads) which makes it possible to vary the quantity of energy delivered and the exponential time constant. The results are presented in Table 4.

TABLE 4

Factor for increase in the expression (luciferase activity) obtained by applying a pulse with exponential decrease. The increase factor is calculated with reference to the luciferase activity obtained with the administration of the plasmid pXL3031 without electrotransfer (mean values of the increase factor, N = 4 to 6 per condition).

| | Capa μF 150 | Capa μF 300 | Capa μF 450 | Capa μF 600 | Capa μF 1200 | Capa μF 2400 | Capa μF 3000 |
|---|---|---|---|---|---|---|---|
| 40 V/cm | | | | | | 1.23 | 11 |
| 100 V/cm | | | | 16.5 | 2.8 | 6.5 | 23.9 |
| 150 V/cm | | | | 1.8 | 3.5 | 6.1 | |
| 200 V/cm | 5.1 | | | 15.8 | 18.8 | 121.5 | 189.7 |

TABLE 4-continued

Factor for increase in the expression (luciferase activity) obtained by applying a pulse with exponential decrease. The increase factor is calculated with reference to the luciferase activity obtained with the administration of the plasmid pXL3031 without electrotransfer (mean values of the increase factor, N = 4 to 6 per condition).

| | Capa μF 150 | Capa μF 300 | Capa μF 450 | Capa μF 600 | Capa μF 1200 | Capa μF 2400 | Capa μF 3000 |
|---|---|---|---|---|---|---|---|
| 300 V/cm | 32.1 | 90.5 | 48.7 | 760.4 | 56.2 | | |
| 400 V/cm | | 795 | | | | | |
| 600 V/cm | 62 | | | | | | |
| 800 V/cm | 3.1 | 1.1 | | | | | |

By way of comparison, the increase in expression factor obtained for the transfer of pXL3031 in the presence of an electric field with square pulses (field intensity of 200 V/cm, 8 pulses of 20 msec, at a frequency of 1 Hertz) was 44 in the same experiment.

These results show that it is possible to use electrical pulses with a square shape or with an intensity which decreases exponentially as a function of time. Furthermore, in the latter case, a substantial increase in expression may be obtained for a low field value and a high capacitance (e.g. 200 V/cm, capacitance 3000 μFarad) or a high field value and a low capacitance (e.g. 400 V/cm, capacitance 300 μFarad).

EXAMPLE 10

Effect of the Combination of a Brief Pulse of High Voltage and Several Long Pulses of Low Voltage This example shows that the electric field delivered may be a combination of at least one field of between 500 and 800 volts/cm for a short duration, for example 50 or 100 μsec, and at least one weak field (<100 volts/cm) for a longer duration, for example ≧1 msec and up to 90 msec in this experiment.

The low electric field values here are 80 V/cm applied as 4 pulses of a duration of 90 msec with a frequency of 1 Hertz. For this experiment, two electropulsators are used. The electrical pulses are applied by one and then the other apparatus, the change being made in less than one second with the aid of a manual control.

The plasmid used is the plasmid pXL3031. The quantity of DNA administered is 3 μg. The electric field values are indicated in Table 5; the other conditions for this experiment are those described in Example 1.

TABLE 5

Mean values +/− SEM of the luciferase activity in millions of RLU per muscle. N = 10 muscles per group.

| Conditions for applying the electric field | Experiment 1 (3 µg pXL3031) | Experiment 2 (3 µg pXL3031) |
|---|---|---|
| Control (absence of electric field) | 320 +/− 126 | 75 +/− 27 |
| A1:500 V/cm, 1 × 0.1 msec | – | 169 +/− 63 |
| A3:800 V/cm, 1 × 0.1 msec | 416 +/− 143 | 272 +/− 84 |
| B:80 V/cm, 4 × 90 msec | 1282 +/− 203 | 362.21 +/− 85.17 |
| Conditions A1 then B | – | 1479 +/− 276 |
| Conditions A3 then B | 3991 +/− 418 | 1426 +/− 209 |
| Conditions B then A3 | – | 347 +/− 66 |

Table 5, which summarizes the results obtained for two series of experiments, shows that a brief high-voltage pulse or that four long and low-voltage successive pulses cause little improvement in transfection relative to the control group which received an injection of pXL3031 but was not subjected to an electric field. The same is true when the weak field pulses are applied before the high field pulse.

On the other hand, in the two series of experiments, the combination of a brief high-voltage pulse followed by four long and low-voltage successive pulses very markedly increases the efficiency of the transfer of DNA.

The results obtained in Examples 1 and 2 showed that 8 pulses of 600, 800 or 1200 volts of a unit duration of 1 msec at 1 Hz caused lesions and inhibited transfection. The results obtained in Example 10 show that, under specific conditions, it is possible to use high-voltage field intensities without causing lesions; indeed, from a macroscopic point of view, the muscles are never visibly impaired. The use of high electric fields of brief duration combined with weak fields of longer duration appears as an additional means of modulating the efficiency of the transfer of DNA.

EXAMPLE 11

Electrotransfer with Plasmids of Different Sizes, Genes Under the Control of Various Promoters or with Sites for Variable Addressing of the Protein Expressed by the Transgene 11.a—Electrotransfer with Plasmids of Different Sizes Plasmids of different size (2.8 Kb, 3.8 Kb, 8.6 Kb, 20 Kb and 52.5 Kb) comprising the gene encoding luciferase were tested. The quantity of plasmid administered is 10 µg per muscle. An electric field with an intensity of 200 V/cm in 8 pulses of 20 msec at 2 Hz is applied, the other conditions for this experiment being those described in Example 1.

An increase in the expression of the transgene of about 50 fold with the 2.8 Kb and 3.8 Kb plasmids, of about 80 fold with the 8.6 Kb plasmid and of 3 to 6 fold with the 20 and 52.6 Kb plasmids is observed.

This example thus demonstrates the possibility of transferring plasmids of large size, of up to 20 Kb and above.

11.b: Control of the Luminescence Signal in the Absence of a Gene Encoding Luciferase.

As a control, and to exclude the possibility that the luminescence signals observed for the assay of the luciferase activity are due to radicals produced in the tissue following the electric treatment, the luciferase activity was tested on muscles treated with a plasmid not encoding luciferase and subjected to an electric field.

TABLE 6

Luciferase activity in muscles injected with various plasmids, with or without application of an electric field. Conditions: 200 V/cm, 8 pulses of 20 msec, frequency 1 Hz. Mean values +/− SEM of the luciferase activity in millions of RLU per muscle.

| | Electrotransfer | |
|---|---|---|
| | − | + |
| Plasmid pXL 3004 (15 µg) encoding β-galactosidase | 0.016 +/− 0.005 (n = 6) | 0.015 +/− 0.006 (n = 6) |
| Plasmid pXL 2774 (15 µg) encoding luciferase | 7.33 +/− 3.53 (n = 10) | 491.71 +/− 122.28 (n = 10) |

The results show that the basal luciferase activity in muscles injected with a plasmid not encoding luciferase is quite negligible.

11.c—Electrotransfer of Genes Under the Control of Various Promoters

The influence of various promoters was tested on the level of expression of the genes transferred, with and without, application of the electric field.

The quantity of plasmid injected per muscle is 2 µg. The electric field applied is 200 V/cm in 8 pulses of 20 msec at 1 Hz, the other conditions for this experiment are those described in Example 1. The results are presented in Table 7. The plasmid tested is the plasmid pXL3031 for the CMV-LUC construct. The PGK construct corresponds to the replacement of the CMV promoter with the PGK promoter in pXL3031.

TABLE 7

Mean values +/− SEM of the luciferase activity in millions of RLU per muscle.

| Promoter | PGK | | CMV | |
|---|---|---|---|---|
| Electrotransfer | − | + | − | + |
| RLU | 8 ± 2.8 | 1070 ± 327 | 157 ± 83 | 20350 ± 1112 |
| Amplification factor | | × 133.7 | | × 129.3 |

These results show that, when the DNA is transferred in the presence of an electric field, the factor for increase in the expression of the transgene is comparable regardless of the origin or the strength of the promoter.

11.d—Electrotransfer of Gene with Various Sites for Addressing the Protein Expressed by the Transgene This example illustrates the transfer of gene encoding proteins having different locations. The plasmid pXL3031 encodes a luciferase synthesized in the cytosol and the plasmid pXL2774 encodes a luciferase addressed in the peroxisomes.

The quantity of plasmid injected per muscle is 10 µg. The electric field applied is 200 V/cm in 8 pulses of 20 msec at 1 Hz, the other conditions for this experiment are those described in Example 1. The results are presented in Table 8.

TABLE 8

Mean values +/- SEM of the luciferase activity in millions of RLU.

| pXL2744 | | pXL3031 | |
|---|---|---|---|
| Electro-transfer − | Electro-transfer + | Electro-transfer − | Electro-transfer + |
| 11 ± 5 | 1158 ± 238 | 839 ± 281 | 111524 ± 16862 |

These results demonstrate that the method according to the invention applies for the transfer of genes encoding proteins with different cell locations, and in particular for peroxisomal proteins or cytosolic proteins.

EXAMPLE 12

Kinetic and Histological Analysis of the Expression of the Transgene 12.a—Kinetics of Expression of the Transgene This example shows that the transfer of nucleic acids in the presence of an electric field under the conditions according to the invention makes it possible to obtain the expression of a transgene at a high and stable level for a period of at least 4 months.

This experiment is carried out with C57B1/6 mice. The plasmid used is the plasmid pXL2774, the quantity of DNA administered is 15 μg. The injection of DNA is followed, or otherwise (control group), by the application of an electric field under the following conditions: intensity 200 V/cm, 8 pulses of 20 msec, frequency 1 Hz. The other conditions for this experiment are those described in Example 1. The luciferase activity is determined on groups of 10 mice sacrificed at various times. The results are presented in FIG. 6.

It is observed, for the control group, that the expression of luciferase is detectable from the 3rd hour after the injection of the plasmid and increases up to the 3rd day (D3) and then decreases notably after 35 days.

It is observed, for the group subjected to the electrical pulses, that the expression of the transgene is maintained at a level which is very markedly higher than that of the control group. Furthermore, in a remarkable manner, it is observed that this level of expression remains high and constant beyond 35 days and at least up to 120 days. This high and sustained level of expression of the transgene is a particularly advantageous result in the perspective of long-term clinical treatments with therapeutic genes.

12.b—Histological Analysis

A histological study was performed under the same conditions but administering the plasmid pCOR CMV-lacZ (pXL3004) encoding the nuclear localization β-galactosidase.

The plasmid pXL3004 (FIG. 13) is a vector derived from the plasmid pXL2774 (WO97/10343) into which the lacZ gene supplemented with a nuclear localization sequence (nls) (Nouvel et al., 1994, Virology 204:180–189)) has been introduced under the control of the CMV promoter of the plasmid pCDNA3 (Invitrogen, The Netherlands) and of the polyadenylation signal of the SV40 virus early region (Genbank SV4CG).

The animals are sacrificed seven days after administration of the plasmid. The histological analysis makes it possible to detect the cells expressing β-galactosidase and whose nucleus is situated in the plane of section (Xgal histochemistry).

The number of muscle fibres having positive nuclei at the level of the sections examined is on average 76 in the group (n=8) which received the plasmid pXL3004 and was then subjected to the electrical pulses, against an average of 8.5 in the control group (n=8) (animals which received the plasmid pXL3004 but which were not subjected to the electrical pulses).

It is observed that the number of muscle fibres expressing the transgene is on average nine times higher compared with the control group. Most of these muscle fibres are quiescent with nuclei situated at the periphery. Very rare centronucleated muscle fibres express β-galactosidase. It is also observed that along the path of injection of the plasmid, the density of positive muscle fibres per unit of surface is greater in the group treated by electrotransfer compared with the control group.

These results as a whole show that, compared with muscles not subjected to an electric field, electrotransfer allows a very marked increase in the number of muscle fibres expressing the transgene as well as a very marked increase in the surface of the region expressing the transgene. It is also observed that the application of the electric field does not cause a notable inflammatory reaction.

EXAMPLE 13

Effect of the Time of Injection of the Nucleic Acid Relative to the Application of the Electric Field This example illustrates the fact that the nucleic acid may be administered at least 30 minutes, and even at least one hour, before the application of the electric field.

This experiment is carried out with C57B1/6 mice. The plasmid used is the plasmid pXL2774. The quantity of DNA administered is 15 μg or 1.5 μg. The injection of DNA is followed, or preceded, by the application of an electric field under the following conditions: intensity 200 V/cm, 8 pulses of 20 msec, frequency 1 Hz. The other conditions for this experiment are those described in Example 1. A control group consists of animals which received an injection of the plasmid but which were not subjected to the electrical pulses. The results are presented in Table 9.

TABLE 9

Mean values +/- SEM of the luciferase activity in millions of RLU per muscle. N = 10 muscles per group.

| Injection of DNA in the absence of electric field | | | | |
|---|---|---|---|---|
| Exp 1 pXL2774 (15 μg) | Exp 2 pXL2774 (15 μg) | Exp 3 pXL2774 (1.5 μg) | Exp 4 pXL2774 (15 μg) | Exp 5 pXL2774 (1.5 μg) |

| Control | 7 ± 4 | 8 ± 6 | 0.4 ± 0.2 | 22 ± 15 | 1 ± 1 |
|---|---|---|---|---|---|

| Injection of DNA in the absence of electric field | | | | |
|---|---|---|---|---|
| Exp 1 pXL2774 (15 μg) | Exp 2 pXL2774 (15 μg) | Exp 3 pXL2774 (1.5 μg) | Exp 4 pXL2774 (15 μg) | Exp 5 pXL2774 (1.5 μg) |

| Control | 7 ± 4 | 8 ± 6 | 0.4 ± 0.2 | 22 ± 15 | 1 ± 1 |
|---|---|---|---|---|---|

| Injection of DNA before application of the electric field | | | | |
|---|---|---|---|---|
| Time | Exp 1 | Exp 2 | Exp 3 | Exp 4 | Exp 5 |

TABLE 9-continued

Mean values +/− SEM of the luciferase activity in millions of RLU per muscle. N = 10 muscles per group.

| | | | | | |
|---|---|---|---|---|---|
| −120 min | | | | 20 ± 5 | 2 ± 1 |
| −60 min | | | | 106 ± 22 | 10 ± 3 |
| −30 min | 303 ± 36 | 237 ± 61 | 7 ± 3 | 184 ± 22 | 15 ± 4 |
| −5 min | 410 ± 7 | | | | |
| −60 sec | 253 ± 51 | | | | |
| −20 sec | 492 ± 122 | 201 ± 43 | 9 ± 3 | 123 ± 23 | 12 ± 2 |

Injection of DNA after application of the electric field

| Time | Exp 1 | Exp 2 | Exp 3 | Exp 4 | Exp 5 |
|---|---|---|---|---|---|
| +10 sec | | | | 7 ± 7 | |
| +20 sec | 11 ± 6 | 0.4 ± 0.1 | | | |
| +60 sec | 8 ± 7 | | | 17 ± 15 | |

The presence of the DNA at the time of application of the electric field is a condition for the efficiency of the electrotransfection. Remarkably, it is observed that the injection of the plasmid can be carried out at least 30 minutes and even 1 hour (experiments 4 and 5) before the application of the electric field and without notably modifying the level of expression. A similar result is obtained both with with a dose of 15 μg of plasmid per muscle and with a 10-fold lower dose of 1.5 μg.

These observations make it possible in particular to envisage multiple injections of the same plasmid, or of different plasmids, at varying times into the muscle prior to the application of the electric field. It is also possible to make multiple injections over a large area of the muscle and then to apply a series of electrical pulses over the entire injected territory to be treated.

EXAMPLE 14

Statistical Study on the Relationship Between the Dose of DNA Injected and the Level of Expression The statistical study presented in this example makes it possible to compare the relationship effect/dose of a transgene administered in the presence, or in the absence, of an electric field. This study also confirms that the method according to the invention considerably reduces the variability of the expression of the transgene.

5-week old C57B16 mice received an injection of plasmid pXL3031 into the cranial tibial muscle and bilaterally. The plasmid doses vary from 0.25 to 32 μg of DNA. Each dose is tested on 10 animals. Immediately after the injection of the plasmid, one of the two legs is subjected to a field of 250 V/cm, with 4 pulses of 20 ms and a frequency of 1 Hz.

The animals are sacrificed 5 days after treatment and the expression of the transgene is evaluated in the tissue extract of each muscle. The results are presented in FIG. 7.

The comparison of the variation of the variances as a function of that of the mean values for each series of ten repeats shows clearly that the distribution of the expression of the transgene is log-normal. The graphical analysis of the results in FIG. 7, confirmed by calculation, shows that the expression varies linearly with the logarithm of the dose of DNA injected.

The Cochran test shows that homogeneity of the variances exists for each regression (with and without electrotransfer), which makes it possible to use the residual variances to carry out all the calculations.

A test of linearity deviation is not significant at the 5% risk in the case where there was electrotransfer; on the other hand, there is a very significant linearity deviation ($p<0.01$), which reflects a high heterogeneity of the responses in the absence of electrotransfer. The residual variance is 5 times lower with electrotransfer.

Taking into account the estimated values of the residual variances, it is possible to use 5 times fewer animals in order to obtain the same power in a test of comparison of transfection efficiency depending on whether electrotransfer is applied or not. Thus, to demonstrate a difference in expression of a factor of 2, 5 or 10, with a confidence interval $P=95\%$, 33, 8 or 5 animals respectively will be needed if the transgene is administered by electrotransfer and 165, 40 or 25 animals respectively in the absence of electrotransfer. A table is presented below summarizing this type of calculation in the case where electrotransfer is used.

| Efficiency or expression ratio | $P = 95\%$ | $P = 90\%$ | $P = 85\%$ | $P = 75\%$ |
|---|---|---|---|---|
| 2 | 33 | 28 | 24 | 19 |
| 5 | 8 | 7 | 6 | 6 |
| 10 | 5 | 5 | 4 | 4 |

Thus, the reduction in the interindividual variability obtained with electrotransfer makes it possible to carry out precise analytical studies on the comparison of the expression of various genes. It also allows a better definition of the treatment doses and should prevent the risk linked to exceeding the doses acceptable in the therapeutic window.

The test of comparison of the slopes obtained for each regression is not significant. It is therefore possible to consider at the 5% risk that there is a parallel between the two regressions.

The calculation of the relative power shows that to achieve a level of expression comparable to that obtained in the presence of electrotransfer, about 250 times more injected DNA is required per muscle in the absence of electrotransfer (243+/−85; confidence interval $P=95\%$).

The calculation of the relative power shows correlatively that, for a given quantity of DNA, the level of expression is about 500 times higher in the presence of electrotransfer compared with the level of expression obtained in the absence of electrotransfer.

EXAMPLE 15

Comparison of Various Types of Electrodes

The aim of this example is to compare the effect of two types of electrodes, plate electrodes and needle electrodes, on the efficiency of the transfer of nucleic acids. The needle electrodes were also tested in various implantation orientations.

The plasmid pXL2774 (150 μg) is injected into the triceps muscle in rats. The plate electrodes are placed as indicated in Example 1. The inter-electrode distance for the plate electrodes is 1.2 cm. For the needle electrodes, the inter-electrode distance is 0.9 cm. The needle electrodes are embedded in the muscle tissue over an equivalent length, either perpendicularly or parallel to the axis of the fibres, on either side of the site of injection. Regardless of the type of electrodes, or their orientation, the conditions for applying the electric field are the following: intensity 200 V/cm, 8 pulses of 20 msec at 2 Hz. The results are presented in FIG. 8.

The results obtained show that the application of the electric field with the aid of two parallel needles implanted in the muscle gives results comparable to what is obtained with plate electrodes placed in contact with the skin surrounding the muscle. It is also shown that the electrotransfer efficiency is independent of the direction of implantation of the needle electrodes relative to the axis of the muscle fibres.

This example shows that the method according to the invention allows the electrotransfer of nucleic acids with the aid of external or invasive electrodes, regardless of their orientation. The use of the needle electrodes is particularly advantageous to ensure the transfer of nucleic acids into muscles which are large in size while retaining moderate-voltage electrical pulses (for example 100 V with a gap of 0.5 cm to deliver an electric field of 200 V/cm).

EXAMPLE 16

Efficiency of Electrotransfer on Various Muscles from Mice, Rats, Rabbits and Monkeys This example illustrates that the electrotransfer of nucleic acids is applicable to various types of muscles, in various mammalian species (mice, rabbits, rats and monkeys).

The conditions for applying the electric field are defined in Table 10 A opposite each species. The results are presented in Table 10 A.

The electrotransfer was also tested in monkeys (*Macaca fascicularis*). The plasmid used is the plasmid pXL3179 comprising the gene encoding the fibroblast growth factor 1 (FGF1 or aFGF).

The plasmid pXL3179 (FIG. 11) is a vector derived from the plasmid pXL2774 (WO97/10343) into which the gene encoding a fusion between the human fibroblast interferon signal peptide and the cDNA for FGF1 (Fibroblast Growth Factor1) (sp-FGF1, Jouanneau et al., 1991 PNAS 88:2893–2897) was introduced under the control of the promoter obtained from the human cytomegalovirus early region (hCMV IE) and the polyadenylation signal of the SV40 virus late region (Genbank SV4CG).

The presence of FGF1 is determined by immunohistochemistry. The values indicate the number of positive sections 3 days after intramuscular injection of 500 µg of the plasmid pXL3179. The conditions for applying the electric field are the following: intensity of the electric field 200 V/cm, 8 pulses of 20 msec at 1 Hz. The results are presented in the table below.

TABLE 10 B

Demonstration, by immunohistochemistry, of the expression of FGF1 in various monkey (*Macaca fascicularis*) muscles. The values indicate the number of positive sections 3 days after intramuscular injection of 500 µg of the plasmid pXL3179 encoding FGF1 with or without electrotransfer.

| Muscle | Electrotransfer – | Electrotransfer + |
|---|---|---|
| Triceps | 0 | 0 |
| Cranial tibial | 0 | 30 |
| Biceps | 0 | 4 |
| Quadriceps | 0 | 30 |

These results demonstrate that electrotransfer remarkably increases the expression of a transgene, in various types of muscles, in various mammalian species.

EXAMPLE 17

Efficiency of Electrotransfer on Rat Diaphragm Muscle

The possibility of sustainably and stably expressing genes of therapeutic interest directly at the level of the diaphragm is a therapeutic approach which is particularly advantageous in the context of the treatment of certain degenerative diseases which affect the functioning of this muscle, such as in particular Duchenne's myopathy.

The rats are anaesthetized with a largactyl and ketamine mixture (1 mg/kg largactyl, 150 mg/kg ketamine). In these experiments, the diaphragm is made accessible by an incision along the sternum. The injection is made into the hemidiaphragm (50 µg of plasmid pXL2774 in 50 µl of 20

TABLE 10A

Factor of increase in expression of luciferase obtained with electrotransfection. This factor is calculated with reference to the luciferase activity obtained for the injection of the plasmid pXL3031 or pXL2774 without electrotransfer. Mean values on 10 muscles per group. The luciferase activity is assayed 7 days after the administration of the plasmid.

| Species | Plasmid | Electrical pulses | Cranial tibial muscle | Gastrocnemius muscle | Rectus muscle of thigh | Triceps muscle of arm | Quadriceps muscle |
|---|---|---|---|---|---|---|---|
| Mouse | 10 µg pXL3031 | 8 × 200 V/cm 20 msec, 2 Hz | × 28 | × 196 | × 342 | × 1121 | |
| Rat | 150 µg pXL3031 | 8 × 200 V/cm 20 msec, 2 Hz | × 31 | | | × 160 | × 13.2 |
| Rabbit | 200 µg pXL2774 | 4 × 200 V/cm 20 msec, 1 Hz | × 25417 | | | × 724 | × 3595 | mM NaCl and 5% glucose). The plate electrodes are then placed on either side of the plane of the diaphragm along the injection path (inter-electrode distance=1 mm). The electrotransfer conditions are the following: field intensity 160 V/cm or 300 V/cm, 8 pulses of 20 msec., frequency 1 hertz. The electric field is applied less than one minute after the injection. The animal is then stitched up.

TABLE 11

Mean values +/– SEM of the luciferase activity in millions of RLU per muscle. N = 12 for each group.

| V/cm | 0 | 160 | 300 |
|---|---|---|---|
| Total RLU | 48 ± 33 | 920 ± 474 | 51 ± 29 |

This example shows a significant improvement in the expression of the transgene in the diaphragm after application of 8 pulses of 20 msec having a field intensity of 160 V/cm ($p<0.003$ with the Mann-Whitney non-parametric test).

EXAMPLE 18

Transfer of a Gene Encoding Secreted Alkaline Phosphatase (SeAP) and Kinetics of Expression of SeAP This example illustrates the capacity of the method according to the invention to transform the muscle into an organ secreting a polypeptide of therapeutic or vaccinal interest and to ensure the presence of a high and stable concentration of the polypeptide of interest in the blood stream.

In this example, the electrotransfer method was tested on adult mice with a plasmid comprising the gene encoding human placental secreted alkaline phosphatase. Adult C57BL6 mice received, in the cranial tibial muscle and unilaterally, an injection of plasmid pXL3010.

The plasmid pXL3010 (FIG. 13) is a vector derived from ColE1 into which the gene encoding secreted alkaline phosphatase obtained from pSEAP-basic (Clontech, Genbank: CVU09660) has been introduced under the control of the CMV promoter obtained from the plasmid pCDNA3 (Invitrogen, the Netherlands) and of the polyadenylation signal of the SV40 virus late region (Genbank SV4CG).

The electrotransfer conditions are the following: electric field 200 V/cm, 8 pulses of 20 msec, frequency 1 Hz. The electric field is applied 20 seconds after injection. The blood samples are collected 7 days later at the level of the retroorbital plexus. The alkaline phosphatase concentration in the serum is performed is measured with the aid of a chemiluminescence test (Phospha-light, Tropix, Bedford, Mass. 01730). The injection of a noncoding plasmid (pUC19) into the muscle, followed or otherwise by the application of an electric field, makes it possible to verify the absence of signal corresponding to the endogenous alkaline phosphatase activity. The results are presented in Table 12.

TABLE 12

Mean values ± SEM of the circulating alkaline phosphatase (SeAP) concentration in the blood in ng/ml of serum.

| Plasmid pXL3010 µg | Plasmid pUC19 µg | Electrotransfer – | Electrotransfer + |
|---|---|---|---|
| 0.1 | 0 | 0.03 ± 0.01 (n = 5) | 1.23 ± 0.21 (n = 10) |
| 0.3 | 0 | 0.05 ± 0.02 (n = 5) | 1.92 ± 0.33 (n = 10) |
| 1 | 0 | 0.16 ± 0.04 (n = 5) | 7.58 ± 1.18 (n = 10) |
| 10 | 0 | 1.52 ± 0.59 (n = 10) | 262.84 ± 54.97 (n = 10) |
| 400 | 0 | 15.64 ± 10.77 (n = 5) | 2203.11 ± 332.34 (n = 5) |
| 0.1 | 9.9 | 0.088 ± 0.015 (n = 5) | 21.39 ± 3.54 (n = 10) |
| 0.3 | 9.7 | 0.90 ± 0.49 (n = 5) | 95.67 ± 16.15 (n = 10) |
| 1 | 9 | 0.26 ± 0.09 (n = 5) | 201.68 ± 32.38 (n = 10) |
| 10 | 0 | 0.21 ± 0.05 (n = 10) | 357.84 ± 77.02 (n = 10) |

When the plasmid pXL3010 is administered by electrotransfection, an increase by a factor of 140 or 170 in the blood SeAP concentration is observed.

The injection of 400 µg of plasmid (injection of 100 µg of DNA into the cranial tibial muscle bilaterally and as two applications at 30 minutes interval before application of the electric field) makes it possible to reach with the electrotransfer a serum concentration of alkaline phosphatase of 2200 ng/ml against 16 ng/ml in the absence of electrotransfer.

It should be noted that the addition of a noncoding DNA (pUC19) which makes it possible to work at a constant quantity of DNA (10 µg of total DNA per mouse) also makes it possible to improve the level of expression of alkaline phosphatase for small quantities of plasmid pXL3010 injected ($\leq 1$ µg).

A kinetics of expression of SeAP was carried out. The dose of plasmid administered is 15 µg per muscle bilaterally, that is to say 30 µg per mouse. The results are presented in FIG. 9. A large and sustainable (for at least 2 months) increase in the concentration of SeAP detected in the blood is observed from 7 days after injection when the plasmid pXL3010 is administered by electrotransfer.

All these results confirm that the transfer of nucleic acids into the muscle with the method according to the invention makes it possible to obtain a high and sustainable level of expression, both for proteins located in the muscle and for secreted proteins and that it is thus possible to transform the muscle into an organ secreting a polypeptide of interest.

EXAMPLE 19

Transfer of a Gene Encoding Erythropoietin (EPO)

Adult C57B1/6 mice received, in the cranial tibial muscle and unilaterally, an injection of plasmid pXL3348. The plasmid pXL3348 (FIG. 16) is a vector derived from the plasmid pXL2774 into which the murine gene for erythropoietin (NCBI: 193086) has been introduced under the control of the promoter obtained from the human cytomegalovirus early region (hCMV IE) and of the polyadenylation signal of the SV40 virus late region (Genbank SV4CG).

The electrotransfer conditions are the following: electric field intensity 200 V/cm, 8 pulses of 20 msec, frequency 1 Hz. The electric field is applied immediately after injection of the plasmid DNA.

TABLE 13

Mean values ± SEM. N = 4 to 5.

| Plasmid | Serum erythropoietin (mIU/ml) at D7 | | Serum erythropoietin (mIU/ml) at D24 | |
|---|---|---|---|---|
| | Electrotransfer – | Electrotransfer + | Electrotransfer – | Electrotransfer + |
| pXL3348 (1 µg) | 0 | 3.0 ± 1.6 | 0 | 1.12 ± 0.08 |
| pXL3348 (10 µg) | 0.9 ± 0.9 | 61.8 ± 15.8 | 0 | 74.1 ± 28.9 |
| pUC19 (1 µg) | | 0 | | 0 |

TABLE 13-continued

Mean values ± SEM. N = 4 to 5.

| | Haematocrit % Collection of sample at D7 | | Haematocrit % Collection of sample at D24 | |
|---|---|---|---|---|
| Plasmid | Electrotransfer − | Electrotransfer + | Electrotransfer − | Electrotransfer + |
| pXL3348 (1 µg) | 38.5 ± 0.5 | 35.0 ± 3.6 | 50.8 ± 2.3 | 81 ± 0.5 |
| pXL3348 (10 µg) | 32.0 ± 3.2 | 26.0 ± 4.1 | 69.0 ± 5.1 | 83.0 ± 1.0 |
| PUC 19 (1 µg) | | 30.8 ± 2.3 | | 43.2 ± 0.9 |

A very marked increase in the quantity of erythropoietin in the blood at D7 and D24 is observed, with the electrotransfer, for the administration of 10 µg of pXL3348. Furthermore, the physiological effect of the increase in erythropoietin which results in an increase in the haematocrit is very high (85%), from D7, this being so even for a very small quantity of plasmid (1 µg).

EXAMPLE 20

Transfer of a Gene Encoding the Vascular Endothelium Growth Factor (VEGF)

Adult C57B16 or SCID mice received, in the cranial tibial muscle and bilaterally, an injection of pCOR hVEGF (pXL3212, 15 µg).

The plasmid pXL3212 (FIG. 11) is a vector derived from the plasmid pXL2774 (WO97/10343) into which the cDNA encoding VEGF165 (Vascular Endothelial Growth Factor, Genbank: HUMEGFAA) has been introduced under the control of the promoter obtained from the human cytomegalovirus early region (hCMV IE) and of the polyadenylation signal of the SV40 virus late region (Genbank SV4CG).

The electrotransfer conditions are the following: electric field intensity 250 V/cm, 8 pulses of 20 msec, frequency 2 Hz. The blood samples were collected at the level of the retroorbital plexus. The samples were collected a day before, and seven days after, the injection of the plasmid. The immunoenzymatic assay of the human VEGF was carried out with the aid of the Quantikine kit (R&D System). The test was calibrated with human VEGF in mouse serum. The results are presented in Table 14.

TABLE 14

Serum VEGF concentration (ng/liter) in C57B16 and SCID mice.

| Mouse line | Day of assay | Electrotransfer | Human VEGF (ng/liter) |
|---|---|---|---|
| C57BL6 | D − 1 | − | not detectable |
| C57BL6 | D + 7 | + | 393 ± 110 |
| SCID | D − 1 | − | not detectable |
| SCID | D + 7 | + | 99 ± 26 |

EXAMPLE 21

Transfer of a Gene Encoding Factor IX

Adult C57B16 or SCID mice received, in the cranial tibial muscle and bilaterally, an injection of pXL3388 (15 µg).

The plasmid pXL3388 (FIG. 12) is a vector derived from the plasmid pXL2774 (WO97/10343) into which the cDNA encoding human factor IX (Christmas factor), Genbank: HUMFIXA) has been introduced under the control of the promoter obtained from the human cytomegalovirus early region (hCMV IE, Genbank HS5IEE) and of the polyadenylation signal of the SV40 virus late region (Genbank SV4CG).

The electrotransfer conditions are the following: electric field intensity 200 V/cm, 8 pulses of 20 msec., frequency 2 Hz. The blood samples were collected at the level of the retroorbital plexus. The samples were collected seven days after injection of the plasmid. The results are presented in Table 15.

TABLE 15

Plasma concentration of factor IX in C57B16 and SCID mice.

| Mouse line | Injection | Electrotransfer | Human factor IX (µg/L) |
|---|---|---|---|
| C57BL/6 | pXL3388 | + | 69 ± 12 |
| C57BL/6 | pXL3388 | − | not detectable |
| C57BL/6 | NaCl 0.9% | + | not detectable |
| SCID | pXL3388 | + | 66 ± 5 |
| SCID | pXL3388 | − | not detectable |

The human factor IX is detectable in the blood only when the plasmid was administered under the conditions of the method according to the invention.

EXAMPLE 22

Transfer of a Gene Encoding the Fibroblast Growth Factor 1 (FGF1)

Adult C57BL6 or SCID mice received, in the cranial tibial muscle and bilaterally, an injection of pCOR FGF1 (pXL3096, 15 µg).

The plasmid pXL3096 (FIG. 14) is a vector derived from the plasmid pXL2774 (WO97/10343) supplemented with a sequence capable of forming a triple helix (T H, Wils et al., 1997. Gene Ther 4:323–330) into which the gene encoding a fusion between the human fibroblast interferon signal peptide and the cDNA for FGF1 (Fibroblast Growth Factor1) (sp-FGF1, Jouanneau et al., PNAS 88:2893–2897) has been introduced under the control of the promoter obtained from the human cytomegalovirus early region (hCMV IE) followed by the leader sequence (transcribed, untranslated) of the HSV1 TK gene and the polyadenylation signal of the SV40 virus late region (Genbank SV4CG).

The electrotransfer conditions are the following: electric field intensity 200 V/cm, 8 pulses of 20 msec., frequency 2 Hz. The presence of FGF1 is then revealed by immunohistochemistry.

The results of the C57BL6 mice are presented in FIG. 10. It is observed that the number of positive fibres is very substantially higher for the group subjected to the electric field compared with the control group (which received an injection of pXL3096 but not subjected to the electric field). The presence of FGF1 for the control group is practically undetectable at D21 and D35 whereas a large number of positive fibres remain observable for the groups treated by electrotransfer.

The results for the SCID mice are presented in Table 16.

TABLE 16

Expression of FGF, immunohistochemical study and number of positive fibres on a muscle section taken in the median part of the muscle

|  | Electrotransfer | Left cranial tibial | Right cranial tibial |
|---|---|---|---|
| pXL 3096 | + | 600 | 450 |
| (15 µg) | + | 700 | 300 |
| pXL 3096 | – | 3 | 0 |
| (15 µg) | – | 3 | 0 |
|  | – | 0 | 0 |
| pXL 3096 | + | 80 | 70 |
| (1.5 µg) | + | 20 | 35 |
|  | + | 110 | 100 |
| pXL 3096 | – | 0 | 0 |
| (1.5 µg) | – | 0 | 1 |

The expression of FGF1, as determined by the number of positive fibres revealed by immunohistochemistry, is detected only in the muscles subjected to the electric field. It should be noted that expression of FGF1 is detected even for a low dose of plasmid administered (1.5 µg).

EXAMPLE 23

Transfer of a Gene Encoding the Neurotrophic Factor NT3

The method according to the invention was applied to adult mice (C57Bl6) and young mice Xt/pmn for the transfer of the gene encoding neurotrophin 3 (NT3). The pmn mice constitute a murine model of amyotrophic lateral sclerosis (ALS) characterized by a premature and rapid degeneration of the motoneurons and by an average life expectancy of about 40 days.

23.1—Transfer of the Gene Encoding NT3 into Adult Mice

Five-week old C57B1/6 mice received, in the cranial tibial muscle and unilaterally, an injection of plasmid pXL3149 (12.5 µg) comprising the gene encoding murine neurotrophin 3 (NT-3).

The plasmid pXL3149 (FIG. 14) is a vector derived from the plasmid pXL2774 (WO97/10343) into which the gene encoding murine neurotrophin 3 (NT-3) (Genbank MMNT3) has been introduced under the control of the promoter obtained from the human cytomegalovirus early region (hCMV IE) and of the polyadenylation signal of the SV40 virus late region (Genbank SV4CG).

The electrotransfer conditions are the following: electric field intensity 250 V/cm, 4 pulses of 20 msec., frequency 1 Hz. The electric field is applied immediately after injection of the plasmid DNA. The presence of NT3 is evaluated in the 12 000 g supernatant of the ground muscle products in PBS buffer 7 days after treating the mice. The quantity of NT3 is measured by an ELISA assay [Promega kit].

The mean values (±95% confidence interval) on 20 muscles are 75+/−11 pg/muscle (plasmid DNA administered without electrotransfer) and 2700+/−900 pg/muscle (plasmid DNA administered with electrotransfer).

An increase by a factor of 55 in the quantity of NT3 produced in the muscle is thus observed when the plasmid pXL3149 is transferred under the conditions of the method according to the invention.

23.2—Transfer of the Gene Encoding NT3 into Young Mice

A comparable experiment was carried out on 4- to 5-day-old heterozygous Xt pmn mice with the plasmid pXL3149. The doses injected are 130 µg per animal and the injections are carried out on a multisite basis into various muscles of the animal (gastrocnemius 25 µg, cranial tibial 12.5 µg).

The electrotransfer conditions are the following: electric field intensity 500 V/cm, 4 pulses of 20 msec, frequency 1 Hz.

The presence of NT3 is evaluated 7 days after administration of the plasmid in the plasma and in the muscle (gastrocnemius or cranial tibial). A control for the basal level of NT3 is obtained by administering a 0.9% NaCl solution. The quantity of NT3 is determined by an ELISA assay [Promega kit]. The results are presented in Table 17.

TABLE 17

Mean values ± SEM of the quantity of NT3 (pg per muscle and pg per ml of plasma).

|  | NaCl 0.9% | | pXL3149 | |
|---|---|---|---|---|
| Electrotransfer | – | + | – | + |
| Plasma | 0 | 0 | 46 ± 10 | 1599 ± 639 |
|  | (n = 2) | (n = 2) | (n = 4) | (n = 4) |
| Gastrocnemius muscle | 3619 ± 102 | 1619 ± 150 | 3647 ± 1078 | 19 754 ± 3818 |
|  | (n = 4) | (n = 2) | (n = 8) | (n = 8) |
| Cranial tibial muscle | 1415 ± 363 | 1453 ± 375 | 1400 ± 155 | 16 826 ± 3135 |
|  | (n = 4) | (n = 2) | (n = 8) | (n = 8) |

Under the experimental conditions a basal level of the NT3 detection signal is observed in the gastrocnemius muscle and in the cranial tibial muscle. In the absence of electrotransfer, the level of expression of the NT3 gene obtained for the injection of the plasmid pXL3149 is not higher at the basal level of detection of NT3 in the muscle. When the plasmid is administered with the method according to the invention, it is observed that the quantity of NT3 detected in the muscle is very significantly increased. It is also observed that the quantity of NT3 secreted by the muscle and detected in the plasma is very markedly increased under these conditions (increase factor ×35).

These results demonstrate that, for a given quantity of DNA, the method according to the invention makes it possible to very significantly increase the efficiency of transfer of DNA and to obtain, not only in the muscle but also in the plasma, a large increase in the quantity of a neurotrophin such as NT3.

EXAMPLE 24

Transfer of the Gene Encoding Human Growth Hormone

C57B1/6 mice received, in the cranial tibial muscle and unilaterally, an injection of plasmid pXL3353 (10 µg) or of plasmid pXL3354 (10 µg). The plasmid pXL3353 (FIG. 15) is a vector derived from the plasmid pXL2774 into which the entire gene for human growth hormone (hGH XbaI/SphI fragment which extends from the signal for initiation of transcription, BamH1 site, up to 224 bp after the poly A site) has been introduced under the control of the promoter obtained from the human cytomegalovirus early region (hCMV IE) and of the polyadenylation signal of the SV40 virus late region.

The cDNA of the gene for human growth hormone was obtained by reverse transcription of a poly(A+) mRNA library from the human pituitary gland followed by 30 PCR amplification cycles with the following oligonucleotides:

Oligonucleotide complementary to the 5' region:

5'-GGGTCTAGAGCCACCATGGCTACAGGCTCCCGGAC-3'

This oligonucleotide contains a XbaI site and the kozak sequence.

Oligonucleotide complementary to the 3' region:

5'-GGGATGCATTTACTAGAAGCCACAGCTGCCTC-3'

This oligonucleotide contains an NsiI site and the stop codon.

The amplified fragment was introduced into the plasmid pCR2.1 (TA cloning kit, invitrogen) and sequenced. An XbaI/NsiI fragment of 681 bp containing the cDNA for hGH was ligated with the XbaI/NsiI fragment of pXL3353 to generate the plasmid pXL3354 (FIG. 15).

The electrotransfer conditions are the following: electric field intensity 200 V/cm, 8 pulses of 20 msec., frequency 1 Hz. The electric field is applied immediately after injection of the plasmid DNA. The presence of hGH is evaluated, 7 days after treating the mice, in the supernatant of ground muscle products in PBS buffer centrifuged at 12 000 g. The quantity of hGH is measured by an ELISA assay (Boehringer Manheim).

TABLE 18

| | Mean values ± SEM of the hGH protein (picograms)/muscle | | | |
|---|---|---|---|---|
| | Genomic hGH injection (pXL3353) | | hGH cDNA injection (pXL3354) | |
| Electrotransfer | − | + | − | + |
| Cranial tibial muscle | 87.1 ± 9.3 (n = 10) | 1477.6 ± 67.6 (n = 10) | 2820.0 ± 487.5 (n = 10) | 15739.1 ± 915.5 (n = 10) |

These results show that the electrotransfer makes it possible to obtain a very large increase in the human growth hormone. It should be noted that this amplification is also observed with the plasmid containing the entire gene with all its regulatory sequences.

EXAMPLE 25

Effect of the Electrotransfer on the Expression of Vaccinal Transgenes

This example demonstrates that the method according to the invention is also applicable to the transfer of genes encoding vaccinal polypeptides of interest.

The experiment is carried out in 9-week-old female Balb/c mice. The electrodes used are stainless steel plate electrodes 5 mm apart. VR-HA is a plasmid DNA containing the haemagglutinin gene of the influenza virus (strain A/PR/8/34). VR-gB is a plasmid DNA containing the glycoprotein B (gB) gene of the human cytomegalovirus (Towne strain).

The plasmid solution (50 µl of a solution at 20 µg/ml or 200 µg/ml in 0.9% NaCl) is injected longitudinally through the skin into the cranial tibial muscle unilaterally. The electrical pulses are applied 20 sec after administering the plasmid, perpendicularly to the axis of the muscle with the aid of a square pulse generator (electric field intensity 200 V/cm, 8 consecutive pulses of 20 msec. duration, frequency 1 Hz).

For the evaluation of the stimulation of the immune response, the following immunization protocol was followed:

| | |
|---|---|
| D 0 | collection of the preimmune serum |
| D 1 | first injection, plus or minus electrotransfer |
| D 2 | collection of the immune serum |
| D 2 | booster injection, plus or minus electrotransfer |
| D 42 | collection of immune serum |
| D 63 | collection of immune serum |

The blood samples are collected at the level of the retroorbital sinus. The assays of specific antibodies are carried out by ELISA. Each experimental condition is tested on 10 animals injected unilaterally.

The results relating to the titres of antibodies directed against the haemagglutinin of the influenza virus are presented in Table 19A.

TABLE 19a

Titres of antibodies directed against the haemagglutinin of the influenza virus, obtained after injection of 1 or 10 µg of DNA (VR-HA) in the absence or in the presence of electrical pulses. The results are the geometric means for 10 animals (8 animals for the group injected with 1 µg of DNA in the presence of electrical pulses and samples collected at D63) ± standard deviation. The value of p was obtained by comparing in pairs the groups injected in the presence and in the absence of electrical pulses using the Mann-Whitney nonparametric test.

| | Electro-transfer | D0 | D21 | D42 | D63 |
|---|---|---|---|---|---|
| VR-HA (1 µg) | − | <50 | 132 ± 739 | 1201 ± 4380 | 1314 ± 2481 |
| VR-HA (1 µg) (p) | + | <50 | 1121 ± 1237 (0.0135) | 10441 ± 7819 (0.0022) | 8121 ± 5619 (0.0033) |
| VR-HA (10 µg) | − | <50 | 781 ± 666 | 5113 ± 16015 | 4673 ± 8238 |
| VR-HA (10 µg) (p) | + | <50 | 4153 ± 2344 (0.0002) | 74761 ± 89228 (0.0005) | 41765 ± 52361 (0.0007) |

These results show that the titres of antibodies directed against the haemagglutinin of the influenza virus are increased by a factor of about 10 in the groups subjected to electrical pulses. Thus, the mice which received 1 µg of DNA in the presence of electrical pulses have a mean antibody titre slightly higher than that of mice which received 10 µg of DNA in the absence of electrical pulse.

The results relating to the titres of antibodies directed against the human cytomegalovirus glycoprotein B are presented in Table 19B.

TABLE 19B

Titres of antibodies directed against the human cytomegalovirus glycoprotein B (gB), obtained after injection of 10 µg of DNA (VR-gB) in the absence or in the presence of electrical pulses. The results are the geometric means for 10 animals (9 animals for the group injected in the presence of electrical pulses) ± standard deviation. The value of p was obtained by comparing in pairs the groups injected in the presence and in the absence of electrical pulses using the Mann-Whitney nonparametric test.

| | Electro-transfer | D0 | D21 | D42 | D63 |
|---|---|---|---|---|---|
| VR-gB (10 µg) | − | <50 | 73 ± 138 | 755 ± 1766 | 809 ± 1363 |
| VR-gB (10 µg) (p) | + | <50 | 200 ± 119 (0.0558) | 3057 ± 1747 (0.0108) | 2112 ± 1330 (0.0479) |

These results show that the titres of antibodies directed against the human cytomegalovirus glycoprotein B are increased by a factor of 4 at D42, in the group subjected to the electrical pulses. It is also noted that the coefficient of variation is on average three times lower in the groups of animals subjected to the electrical pulses.

What is claimed is:

1. A method of transferring nucleic acids into one or more striated muscles in vivo comprising: contacting in vivo at least one striated muscle cell with at least one nucleic acid, and electrically stimulating said at least one striated muscle cell with at least one unipolar pulse of an electric field intensity ranging from 1 to 800 V/cm and wherein said electric stimulation is greater than 10 milliseconds in duration.

2. The method according to claim 1, wherein said at least one striated muscle cell is a skeletal muscle cell.

3. The method according to claim 1, wherein said at least one nucleic acid is injected by a systemic route.

4. The method according to claim 1, wherein said at least one nucleic acid is injected by an intra-arterial or intravenous route.

5. The method according to claim 1, wherein said electric field intensity ranges from 1 to 200 V/cm.

6. The method according to claim 5, wherein said electric field intensity ranges from 100 to 200 V/cm.

7. The method according to claim 1, wherein said electrical stimulation comprises from 1 to 100,000 unipolar pulses.

8. The method according to claim 1, wherein said at least one unipolar pulse is chosen from square wave pulses and exponentially decreasing pulses.

9. The method according to claim 1, wherein said at least one nucleic acid encodes at least one blood-clotting factor.

10. The method according to claim 9, wherein said blood-clotting factor is chosen from factor VII, factor VIII, and factor IX.

11. The method according to claim 10, wherein said blood-clotting factor is factor IX.

12. The method according to claim 1, wherein said at least one nucleic acid encodes at least one neurotrophic factor.

13. The method according to claim 12, wherein said neurotrophic factor is chosen from NGF, BDNF, NT3, NT4/5, and NT6.

14. The method according to claim 1, wherein said at least one nucleic acid encodes at least one hematopoietic factor.

15. The method according to claim 14, where said at least one hematopoietic factor is chosen from erythropoietin, GM-CSF, M-CSF, and LIF.

16. The method according to claim 1, wherein said at least one nucleic acid encodes human factor IX.

17. The method according to claim 1, wherein said at least one nucleic acid encodes SeAP.

18. The method according to claim 1, wherein said at least one nucleic acid encodes EPO.

19. The method according to claim 1, wherein said at least one nucleic acid encodes VEGF.

20. The method according to claim 1, wherein said at least one nucleic acid encodes FGF1.

21. The method according to claim 1, wherein said at least one nucleic acid encodes NT3.

22. The method according to claim 1, wherein said at least one nucleic acid encodes human growth hormone.

23. The method of claim 1, wherein said at least one nucleic acid encodes at least one angiogenic factor.

24. The method according to claim 23, wherein said angiogenic factor is chosen from VEGF, FGF, angiopoietin 1, angiopoietin 2, and endothelin.

25. The method according to claim 24, wherein said angiogenic factor is VEGF.

26. The method according to claim 24, wherein said angiogenic factor is FGF.

27. The method according to claim 26, wherein said FGF is FGF 1.

28. The method of claim 1, wherein the electric field intensity ranges from 30 to 300 V/cm.

29. The method of claim 1, wherein contacting in vivo at least one striated muscle cell with at least one nucleic acid precedes electrically stimulating said at least one striated muscle cell with at least one unipolar pulse of an electric field intensity ranging from 1 to 800 V/cm.

30. The method of claim 1, wherein the electric field intensity ranges from 1 to 400 V/cm.

* * * * *